United States Patent
Cassayre et al.

(10) Patent No.: US 8,338,443 B2
(45) Date of Patent: *Dec. 25, 2012

(54) CHEMICAL COMPOUNDS

(75) Inventors: Jérôme Cassayre, Basel (CH); Peter Maienfisch, Basel (CH); Fredrik Cederbaum, Basel (CH); Louis-Pierre Molleyres, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 932 days.

This patent is subject to a terminal disclaimer.

(21) Appl. No.: 12/097,936

(22) PCT Filed: Dec. 6, 2006

(86) PCT No.: PCT/IB2006/003585
§ 371 (c)(1),
(2), (4) Date: Sep. 11, 2008

(87) PCT Pub. No.: WO2007/072143
PCT Pub. Date: Jun. 28, 2007

(65) Prior Publication Data
US 2009/0118295 A1 May 7, 2009

(51) Int. Cl.
| | | |
|---|---|---|
| A01N 43/42 | (2006.01) | |
| A01N 43/00 | (2006.01) | |
| A01N 43/62 | (2006.01) | |
| A01N 43/66 | (2006.01) | |
| A01N 43/58 | (2006.01) | |
| A01N 43/60 | (2006.01) | |
| A01N 43/02 | (2006.01) | |
| A01N 43/16 | (2006.01) | |
| A01N 43/30 | (2006.01) | |
| A61K 31/44 | (2006.01) | |
| A61K 31/397 | (2006.01) | |
| A61K 31/00 | (2006.01) | |
| A61K 31/55 | (2006.01) | |
| A61K 31/54 | (2006.01) | |
| A61K 31/535 | (2006.01) | |
| A61K 31/53 | (2006.01) | |
| A61K 31/525 | (2006.01) | |
| A61K 31/50 | (2006.01) | |
| A61K 31/38 | (2006.01) | |
| A61K 31/35 | (2006.01) | |
| A61K 31/36 | (2006.01) | |

(52) U.S. Cl. .................. 514/279; 514/210; 514/211.05; 514/221; 514/222.2; 514/222.5; 514/230.5; 514/241; 514/248; 514/299; 514/359; 514/430; 514/456; 514/464

(58) Field of Classification Search .................. 514/183, 514/210, 211.05, 221, 222.2–222.8, 230.5, 514/241, 248, 299, 359, 430, 456, 464, 279
See application file for complete search history.

(56) References Cited

FOREIGN PATENT DOCUMENTS

| | | |
|---|---|---|
| EP | 0029707 | 6/1981 |
| EP | 0092391 | 10/1983 |
| EP | 1069124 | 1/2001 |
| WO | 2003037271 | 5/2003 |
| WO | 2003037890 | 7/2003 |
| WO | 2003053939 | 7/2003 |
| WO | WO 2004018428 A1 * | 3/2004 |
| WO | 2004075823 | 9/2004 |
| WO | 2005058035 | 6/2005 |
| WO | 2005115146 | 12/2005 |
| WO | 2006003494 | 1/2006 |
| WO | 2006076595 | 7/2006 |
| WO | 2007022305 | 2/2007 |

OTHER PUBLICATIONS

Georgis et al. "Effect of Steinernematid and Heterohanditid Nematodes (Rhanditda: Steinernematidae and Heterohanditidae) on Nontarget Arthropods" Environmental Entomology, Jun. 1991, vol. 20, no. 3, pp. 815-822, abstract provided.*
Knowles, C.O. "Effects of Formamidines on Acarine Dispersal and Reproduction", 1987, in Sites of Action for Neurotoxic Peticides, Acs Symposium Series, American Chemical Society, pp. 174-190.*
Database Caplus [Online]; Chemical Abstracts Service, Columbus Ohio, US; Makara, Gergely M. et al: "Synthesis of Bicyclic Pyrimidine Derivatives as ATP Analogues;" XP002451983, retrieved from STN Database accession No. 2001:538300; CAS-RN 364039-88-3 abstract & Journal of Organic Chemistry, 66(17), 5783-5789 CODEN; JOCEAH; ISSN: 0022-3263, 2001.

(Continued)

Primary Examiner — Sreeni Padmanabhan
Assistant Examiner — Kendra D Carter
(74) Attorney, Agent, or Firm — R. Kody Jones

(57) ABSTRACT

The use of a compound of formula I wherein Y is a single bond, C=O, C=S or $S(O)_m$, where m is 0, 1 or 2; the ring is a 6-membered aromatic or is a 5 or 6 membered heteroaromatic ring; Z and Z' are joined by a single or a double bond and are =C— or —N— provided that both are not N; Ra, $R^1$, $R^2$, $R^3$, $R^{3a}$, $R^4$ and $R^8$ are specified organic groups; n is 2, 3 or 4 and p is 0-4; or salts or N-oxides thereof or compositions containing them in controlling insects, acarines, nematodes or molluscs. Novel compounds are also provided.

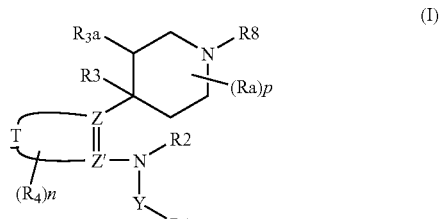

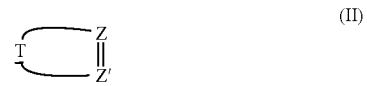

14 Claims, No Drawings

OTHER PUBLICATIONS

Database Caplus [Online]; Chemical Abstracts Service, Columbus Ohio, US; Suzuki, Nobuhiro et al: "Preparation of imidazole derivatives as gonadotropin-releasing hormone antagonists"; XP002451984, retrieved from STN Database Accession No. 2000:214835; CAS-RN 263022-66-8, 263022-67-9 abstract, & JP 2000 095767 A (Takeda Chemical Industries Ltd., Japan), Apr. 4, 2000.

Database Caplus [Online]; Chemical Abstracts Service, Columbus Ohio, US; "Cardiotonic heterocyclic compounds;" XP002451985, retrieved from STN Database accession No. 1986:19604; CAS-RN 99161-55-4 abstract & JP 60 120872 A (Kyowa Hakko Kogyo Co., Ltd., Japan) Jun. 28, 1985.

Database Caplus [Online]; Chemical Abstracts Service, Columbus Ohio, US; Obase, Hiroyuki et al: "Synthesis of cyclic guanidines fused with aromatic ring through metal ion promoted cyclization"XP002451986; retrieved from STN Database accession No. 1984:68253; CAS-RN 88632-10-4, 88632-11-5, 88632-12-6, 87138-50-9, abstract & Bulletin of the Chemical Society of Japan, 56(10), 3189-90 CODEN: BCSJA8; ISSN: 0009-2673, 1983.

Database Caplus [Online]; Chemical Abstracts Service, Columbus Ohio, US; Obase, Hiroyuki et al: Synthesis of (1-substituted piperidin-4-yl)1H-benzimidazoles and (1-substituted piperidin-4-yl)-3,4-dihydroquinazolines as possible antihypertensive agents; XP002451987, retrieved from STN Database accession No. 1983:522375, & Journal of Heterocyclic Chemistry, 20(3), 565-73; CODEN: JHTCAD; ISSN: 0022-152x, 1983.

* cited by examiner

CHEMICAL COMPOUNDS

This application is a 371 of International Application No. PCT/IB2006/003585 filed Dec. 6, 2006, which claims priority to GB 0526042.7 filed Dec. 21, 2005, the contents of which are incorporated herein by reference.

The present invention relates to piperidine derivatives, to processes for preparing them, to insecticidal, acaricidal, molluscicidal and nematicidal compositions comprising them and to methods of using them to combat and control insect, acarine, mollusc and nematode pests.

Piperidine derivatives with fungicidal properties are disclosed in for example in EP494717.

It has now surprisingly been found that certain piperidines have insecticidal properties.

The present invention therefore provides a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I):

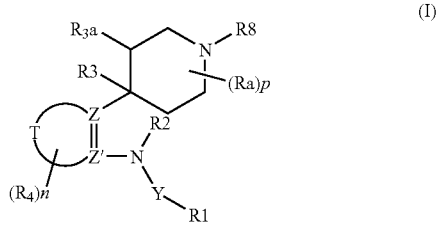

Y is a single bond, C=O, C=S or $S(O)_m$ where m is 0, 1 or 2;
the ring

is a 6 membered aromatic ring or is a 5 or 6 membered heteroaromatic ring;
Z and Z' are joined by a single or a double bond and are

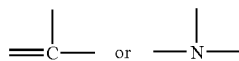

provided that both are not N;

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$ where $R^{13}$ and $R^{14}$ are independently hydrogen, $COR^{15}$, optionally substituted alkyl, optionally substituted aryl, optionally substituted heteroaryl, optionally substituted heterocyclyl or $R^{13}$ and $R^{14}$ together with the N atom to which they are attached form a group $-N=C(R^{16})-NR^{17}R^{18}$ or $R^{13}$ and $R^{14}$ together with the N atom to which they are attached form a five, six or seven-membered heterocyclic ring which may contain one or two further heteroatoms selected from O, N or S and which may be optionally substituted by one or two $C_{1-6}$ alkyl groups; $R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$; $R^{16}$, $R^{17}$ and $R^{18}$ are each independently H or lower alkyl; $R^{19}$ and $R^{20}$ are independently optionally substituted alkyl, optionally substituted aryl or optionally substituted heteroaryl;

$R^2$ is H, hydroxy, optionally substituted alkoxy or optionally substituted alkyl; or $R^1$ and $R^2$ together with the groups Y and N form a 5- or 6-membered heterocyclic ring which may optionally contain one further heteroatom selected from O, N or S and which may be optionally substituted by $C_{1-4}$ alkyl, $C_{1-4}$ haloalkyl or halogen;

$R^3$ is H, OH, halogen or optionally substituted alkyl;
$R^{3a}$ is H or $R^3$ and $R^{3a}$ together form a bond;

two adjacent groups $R^4$ together with the atoms to which they are attached form a 4, 5, 6, or 7 membered carbocyclic, heteroaromatic, or heterocyclic ring optionally carrying one, two or three $R^5$ groups; provided that when the two adjacent $R^4$ groups are both attached to carbon atoms to form a carbocyclic or heterocyclic ring then the resulting carbocyclic or heterocyclic ring is substituted with a substituent other than halogen, $C_{1-8}$ alkoxy, $C_{1-6}$ haloalkoxy, phenoxy (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or $R^{19}R^{20}N$ where $R^{19}$ and $R^{20}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxycarbonyl or $R^{19}$ and $R^{20}$ together with the N atom to which they are attached form a five, six or seven-membered heterocyclic ring which may contain one or two further heteroatoms selected from O, N or S and which may be optionally substituted by one or two $C_{1-6}$ alkyl groups;

optionally any further $R^4$ groups are each independently halogen, nitro, cyano, thiocyanato, optionally substituted C is alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, arylthio, heteroarylthio, alkylsulfoxyl, arylsulfoxyl, heteroarylsulfoxyl, alkylsulfonyl, arylsulfonyl, heteroarylsulfonyl or $R^{23}R^{24}N$ where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl$(C_{1-4})$alkyl, $C_{2-6}$ haloalkyl, $C_{1-6}$ alkoxy$(C_{1-6})$alkyl, $C_{1-6}$ alkoxycarbonyl or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups; n is 2, 3 or 4 each $R^5$ is independently halogen, nitro, cyano, thiocyanato, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, arylthio, heteroarylthio, alkylsulfoxyl, arylsulfoxyl, heteroarylsulfoxyl, alkylsulfonyl, arylsulfonyl, heteroarylsulfonyl or $R^{25}R^{26}N$ where $R^{25}$ and $R^{26}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{25}$ and $R^{26}$ together with the N atom to which they are attached form a five, six or seven-membered heterocyclic ring which may contain one or two further heteroatoms selected from O, N or S and which may be optionally substituted by one or two $C_{1-6}$ alkyl groups;

$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl;

each Ra is independently halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{29}R^{30}N$ where $R^{29}$ and $R^{30}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{29}$ and $R^{30}$ together with the N atom to which they are attached form a five, six or seven-membered heterocyclic ring which may contain one or two further heteroatoms selected from O, N or S and which may be optionally substituted by one or two $C_{1-6}$ alkyl groups, or two Ra groups attached to the same carbon atom are =O, =S, =NRb, =CRcRd where Rb, Rc and Rd are independently H or optionally substituted alkyl; p is 0, 1, 2, 3 or 4 or salts or N-oxides thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are suitably $C_1$ to $C_{12}$ alkyl groups, but are preferably $C_1$-$C_{10}$, more preferably $C_1$-$C_8$, even more preferably $C_1$-$C_6$ and most preferably $C_1$-$C_4$ alkyl groups.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, NCS—, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy ($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)-alkoxy (where the aryl group is optionally substituted), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl ($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$) alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri ($C_{1-4}$)alkylsilyl, aryldi($C_{1-4}$)alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl) aminocarbonyl, N—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), di($C_{1-6}$)alkylaminocarbonyloxy, oximes such as =NOalkyl, =NOhaloalkyl and =NOaryl (itself optionally substituted), aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{2-6}$ alkynylcarbonyl, optionally substituted arylcarbonyl (for example benzoyl) or optionally substituted heteroarylcarbonyl.

Halogen is fluorine, chlorine, bromine or iodine.

Haloalkyl groups are alkyl groups which are substituted with one or more of the same or different halogen atoms and are, for example, $CF_3$, $CF_2Cl$, $CF_3CH_2$ or $CHF_2CH_2$.

In the context of the present specification the terms "aryl", "aromatic ring" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, 2,1,3-benzoxadiazole and thiazolyl.

The terms heterocycle and heterocyclyl refer to a non-aromatic ring containing up to 10 atoms including one or more (preferably one or two) heteroatoms selected from O, S and N. Examples of such rings include 1,3-dioxolane, tetrahydrofuran and morpholine.

When present, the optional substituents on heterocyclyl include $C_{1-6}$ alkyl and $C_{1-6}$ haloalkyl as well as those optional substituents given above for an alkyl moiety.

Cycloalkyl includes cyclopropyl, cyclopentyl and cyclohexyl.

Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups.

When present, the optional substituents on aryl or heteroaryl are selected independently, from halogen, nitro, cyano, NCS—, $C_{1-6}$ alkyl, $C_{1-6}$ haloalkyl, $C_{1-6}$ alkoxy-$(C_{1-6})$alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy$(C_{1-10})$alkoxy, tri$(C_{1-4})$alkyl-silyl$(C_{1-6})$alkoxy, $C_{1-6}$ alkoxycarbonyl$(C_{1-10})$alkoxy, $C_{1-10}$ haloalkoxy, aryl$(C_{1-4})$alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl$(C_{1-4})$alkylthio $C_{3-7}$ cycloalkylthio (where the cycloalkyl group is optionally substituted with $C_{1-6}$ alkyl or halogen), tri$(C_{1-4})$-alkylsilyl$(C_{1-6})$alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, tri$(C_{1-4})$alkylsilyl, aryldi$(C_{1-4})$-alkylsilyl, $(C_{1-4})$alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di$(C_{1-6}$ alkyl)-aminocarbonyl, N—$(C_{1-3}$ alkyl)-N—$(C_{1-3}$ alkoxy)aminocarbonyl, $C_{1-6}$ alkylcarbonyloxy, arylcarbonyloxy, di$(C_{1-6})$alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di$(C_{1-6})$alkylamino, $C_{1-6}$ alkylcarbonylamino, N—$(C_{1-6})$alkylcarbonyl-N—$(C_{1-6})$alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include aryl carbonyl amino (where the aryl group is substituted by $C_{1-6}$ alkyl or halogen), $(C_{1-6})$alkyloxycarbonylamino $(C_{1-6})$alkyloxycarbonyl-N—$(C_{1-6})$alkylamino, aryloxycarbonylamino (where the aryl group is substituted by $C_{1-6}$ alkyl or halogen), aryloxycarbonyl-N—$(C_{1-6})$alkylamino, (where the aryl group is substituted by $C_{1-6}$ alkyl or halogen), arylsulphonylamino (where the aryl group is substituted by $C_{1-6}$ alkyl or halogen), arylsulphonyl-N—$(C_{1-6})$alkylamino (where the aryl group is substituted by $C_{1-6}$ alkyl or halogen), aryl-N—$(C_{1-6})$alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonyl amino, di$(C_{1-6})$alkylaminocarbonyl amino, arylaminocarbonyl amino where the aryl group is substituted by $C_{1-6}$ alkyl or halogen), aryl-N—$(C_{1-6})$alkylaminocarbonylamino where the aryl group is substituted by $C_{1-6}$ alkyl or halogen), $C_{1-6}$ alkylaminocarbonyl-N—$(C_{1-6})$ alkyl amino, di$(C_{1-6})$alkylaminocarbonyl-N—$(C_{1-6})$alkyl amino, arylaminocarbonyl-N—$(C_{1-6})$alkyl amino where the aryl group is substituted by $C_{1-6}$ alkyl or halogen) and aryl-N—$(C_{1-6})$alkylaminocarbonyl-N—$(C_{1-6})$alkyl amino where the aryl group is substituted by $C_{1-6}$ alkyl or halogen).

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy$(C_{1-6})$alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, $R^{31}R^{32}N$ or $R^{33}R^{34}NC(O)$; wherein $R^{31}$, $R^{32}$, $R^{33}$ and $R^{34}$ are, independently, hydrogen or $C_{1-6}$ alkyl. Further preferred substituents are aryl and heteroaryl groups.

Haloalkenyl groups are alkenyl groups which are substituted with one or more of the same or different halogen atoms.

It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected $(C_{1-6})$alkyl groups. When heterocyclic rings are formed by joining two groups on an N atom, the resulting rings are suitably pyrrolidine, piperidine, thiomorpholine and morpholine each of which may be substituted by one or two independently selected $(C_{1-6})$ alkyl groups.

Preferably the optional substituents on an alkyl moiety include one or more of halogen, nitro, cyano, $HO_2C$, $C_{1-10}$ alkoxy (itself optionally substituted by $C_{1-10}$ alkoxy), aryl $(C_{1-4})$alkoxy, $C_{1-10}$ alkylthio, $C_{1-10}$ alkylcarbonyl, $C_{1-10}$ alkoxycarbonyl, $C_{1-6}$ alkylaminocarbonyl, di$(C_{1-6}$ alkyl)aminocarbonyl, $(C_{1-6})$alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with $(C_{1-6})$alkyl or halogen), $C_{3-7}$ cycloalkyloxy, $C_{5-7}$ cycloalkenyl, $C_{1-6}$ alkylsulfonyl, $C_{1-6}$ alkylsulfinyl, tri$(C_{1-4})$alkylsilyl, tri$(C_{1-4})$alkylsilyl$(C_{1-6})$alkoxy, aryldi$(C_{1-4})$alkylsilyl, $(C_{1-4})$alkyldiarylsilyl and triarylsilyl.

Preferably the optional substituents on alkenyl or alkynyl include one or more of halogen, aryl and $C_{3-7}$ cycloalkyl.

A preferred optional substituent for heterocyclyl is $C_{1-6}$ alkyl.

Preferably the optional substituents for cycloalkyl include halogen, cyano and $C_{1-3}$ alkyl.

Preferably the optional substituents for cycloalkenyl include $C_{1-3}$ alkyl, halogen and cyano.

Preferred groups for T, Y, Ra, $R^1$, $R^2$, $R^3$, $R^{3a}$, $R^4$ and $R^8$ in any combination thereof are set out below.

Preferably Y is a single bond, C=O or C=S.

More preferably Y is a single bond or C=O.

Most preferably Y is C=O.

Preferably $R^1$ is hydrogen, $C_{1-6}$ alkyl, $C_{1-6}$ cyanoalkyl, $C_{1-6}$ haloalkyl, $C_{3-7}$ cycloalkyl($C_{1-4}$)alkyl, $C_{1-6}$ alkoxy($C_{1-6}$)alkyl, heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), aryl($C_{1-6}$)alkyl (wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), $C_{1-6}$ alkylcarbonylamino($C_{1-6}$)alkyl, aryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, phenoxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyloxy (optionally substituted by halo, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ alkynyl, $C_{3-6}$ cycloalkyl, $C_{5-7}$ cycloalkenyl, heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl, $C_{1-6}$ haloalkyl, $C_{1-6}$ alkoxy($C_{1-6}$)alkyl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino or $C_{1-4}$ alkoxycarbonyl), phenyl ($C_{1-6}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl ($C_{1-6}$) alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen) or heteroaryl (which may be optionally substituted by halo, nitro, cyano, $C_{1-6}$ alkyl, $C_{1-6}$ haloalkyl, $C_{1-6}$ alkoxy or $C_{1-6}$ haloalkoxy, $C_{1-4}$ alkoxycarbonyl $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), amino, $C_{1-6}$ alkylamino or phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino)).

More preferably $R^1$ is $C_{1-6}$ alkyl, $C_{1-6}$ haloalkyl, $C_{1-6}$ alkoxy($C_{1-6}$)alkyl, heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-14}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, $C_{2-6}$ alkenyl, heterocyclyl (optionally substituted by halo, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl or $C_{1-6}$ haloalkyl, $C_{1-6}$ alkoxy($C_{1-6}$)alkyl, $C_{2-6}$ alkylcarbonyl, phenylcarbonyl, (where the phenyl is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen) or heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen).

Even more preferably $R^1$ is $C_{1-6}$ alkyl, $C_{1-6}$ haloalkyl, heteroaryl($C_{1-3}$)alkyl (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring), heteroaryl (optionally substituted by halo, cyano, $C_{1-6}$ alkyl, $C_{1-6}$ haloalkyl and where the heteroaryl group is a pyridine, pyrimidine, 2,1,3-benzoxadiazole, pyrazine or pyridazine ring), $C_{1-6}$ alkoxy, $C_{1-6}$ alkoxy($C_{1-6}$)alkyl, $C_{1-6}$ alkylamino, $C_{1-6}$ alkyoxy($C_{1-6}$)alkylamino or heteroaryl($C_{1-3}$)alkylamino (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring).

Most preferably $R^1$ is pyridyl (optionally substituted by halo, $C_{1-3}$ alkyl or $C_{1-3}$ haloalkyl) especially halo-substituted pyridyl.

It is preferred that $R^2$ is hydrogen, hydroxy, $C_{1-6}$ alkyl or $C_{1-6}$ haloalkyl.

More preferably $R^2$ is hydrogen, $C_{1-4}$ alkyl or $C_{1-4}$ haloalkyl.

Even more preferably $R^2$ is hydrogen or $C_{1-4}$ alkyl.

Yet more preferably $R^2$ is independently hydrogen or methyl.

Most preferably $R^2$ is hydrogen.

It is preferred that $R^3$ is hydrogen, hydroxy, halogen, $C_{1-6}$ alkyl or $C_{1-6}$ haloalkyl.

More preferably $R^3$ is hydrogen, hydroxy, halogen, $C_{1-4}$ alkyl or $C_{1-4}$ haloalkyl.

Even more preferably $R^3$ is hydrogen or $C_{1-4}$ alkyl.

Yet more preferably $R^3$ is independently hydrogen or methyl.

Most preferably $R^3$ is hydrogen.

$R^{3a}$ is preferably hydrogen or $R^3$ and $R^{3a}$ together form a double bond.

It is preferred that when two adjacent groups $R^4$ together with the atoms to which they are attached in ring

form a ring then the resulting fused ring system formed from ring T and the $R^4$ groups is preferably a 5,6 or 6,6 fused ring wherein the ring members are each independently CH, S, N, $NR^5$, O, or $CR^5$ where $R^5$ is as defined above provided that there are no more than one O or S atoms present in the ring.

More preferably when 2 adjacent groups $R^4$ together with the atoms to which they are attached in ring

form a ring then the resulting fused ring system formed from ring T and the $R^4$ groups is naphthalene, quinoline, quinazoline, quinoxaline, cinnoline, pyridopyrimidine, pyridopyrazine, pyridopyridazine, benzothiophene, indole, benzofuran, benzimidazole, indazole, benzoxazole, benzothiazole, benzisoxazole, benzisothiazole, benzotriazole, benzoxadiazole, benzothiadiazole, thienopyridine, thiazolopyridine, imidazopyridine, pyrazolopyridine or triazolopyridine Most preferably when 2 adjacent groups $R^4$ together with the atoms to which they are attached in ring

form a ring then the resulting fused ring system formed from ring T and the $R^4$ groups is naphthalene, quinoline, benzothiophene, indole, benzofuran, benzimidazole, indazole, benzoxazole or benzothiazole.

Preferably each $R^5$ is independently halogen, cyano, $C_{1-8}$ alkyl, $C_{1-8}$ haloalkyl, $C_{1-6}$ cyanoalkyl, $C_{1-6}$ alkoxy$(C_{1-6})$ alkyl, $C_{3-7}$ cycloalkyl$(C_{1-6})$alkyl, $C_{5-6}$ cycloalkenyl$(C_{1-6})$alkyl $C_{3-6}$ alkenyloxy$(C_{1-6})$alkyl, $C_{3-6}$ alkynyloxy$(C_{1-6})$alkyl, aryloxy$(C_{1-6})$alkyl, $C_{1-6}$ carboxyalkyl, $C_{1-6}$ alkylcarbonyl$(C_{1-6})$alkyl, $C_{2-6}$ alkenylcarbonyl$(C_{1-6})$alkyl, $C_{2-6}$ alkynylcarbonyl$(C_{1-6})$-alkyl, $C_{1-6}$ alkoxycarbonyl$(C_{1-6})$ alkyl, $C_{3-6}$ alkenyloxycarbonyl$(C_{1-6})$alkyl, $C_{3-6}$ alkynyloxycarbonyl$(C_{1-6})$alkyl, aryloxycarbonyl$(C_{1-6})$alkyl, $C_{1-6}$ alkylthio$(C_{1-6})$alkyl, $C_{1-6}$ alkylsulfinyl$(C_{1-6})$alkyl, $C_{1-6}$ alkylsulfonyl$(C_{1-6})$alkyl, aminocarbonyl$(C_{1-6})$alkyl, $C_{1-6}$ alkylaminocarbonyl$(C_{1-6})$alkyl, di$(C_{1-6})$alkylaminocarbonyl $(C_{1-6})$alkyl, phenyl$(C_{1-4})$alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl$(C_{1-4})$alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl$(C_{1-4})$alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, aminocarbonyl$(C_{2-6})$alkenyl, $C_{1-6}$ alkylaminocarbonyl$(C_{2-6})$alkenyl, di$(C_{1-6})$alkylaminocarbonyl$(C_{2-6})$alkenyl, phenyl$(C_{2-4})$-alkenyl, (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkynyl, trimethylsilyl$(C_{2-6})$alkynyl, aminocarbonyl$(C_{2-6})$alkynyl, $C_{1-6}$ alkylaminocarbonyl$(C_{2-6})$ alkynyl, di$(C_{1-6})$alkylaminocarbonyl$(C_{2-6})$alkynyl, $C_{1-6}$ alkoxycarbonyl, $C_{3-7}$ cycloalkyl, $C_{3-7}$ halocycloalkyl, $C_{3-7}$ cyanocycloalkyl, $C_{1-3}$ alkyl$(C_{3-7})$-cycloalkyl, $C_{1-3}$ alkyl $(C_{3-7})$halocycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy).

More preferably each $R^5$ is independently halogen, cyano, $C_{1-8}$ alkyl, $C_{1-8}$ haloalkyl, $C_{1-8}$ cyanoalkyl, $C_{1-6}$ alkoxy$(C_{1-6})$ alkyl, $C_{2-6}$ alkynyl, trimethylsilyl$(C_{2-6})$alkynyl, $C_{1-6}$ alkoxycarbonyl, $C_{3-7}$ cycloalkyl, $C_{1-3}$ alkyl $(C_{3-7})$ cycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkoxy, $C_{1-6}$ haloalkoxy, phenoxy (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-3}$ alkyl, $C_{1-3}$ haloalkyl, $C_{1-3}$ alkoxy or $C_{1-3}$ haloalkoxy), di$(C_{1-8})$alkylamino.

Even more preferably each $R^5$ is independently halogen, cyano, $C_{1-8}$ alkyl, $C_{1-8}$ haloalkyl, $C_{1-8}$ cyanoalkyl, $C_{1-6}$ alkoxy$(C_{1-6})$alkyl, $C_{2-6}$ alkynyl, heterocyclyl (optionally substituted by $C_{1-6}$ alkyl), $C_{1-8}$ alkoxy, $C_{1-6}$ haloalkoxy, phenoxy (optionally substituted by halo, cyano, $C_{1-3}$ alkyl or $C_{1-3}$ haloalkyl), heteroaryloxy (optionally substituted by halo, cyano, $C_{1-3}$ alkyl or $C_{1-3}$ haloalkyl), di$(C_{1-8})$alkylamino.

Yet more preferably each $R^5$ is independently fluoro, chloro, bromo, cyano, $C_{1-4}$ alkyl, $C_{1-4}$ haloalkyl, $C_{1-4}$ cyanoalkyl or $C_{1-3}$ alkoxy$(C_{1-3})$alkyl.

Most preferably each $R^5$ is independently fluoro, chloro, bromo, $C_{1-4}$ alkyl or $C_{1-4}$ haloalkyl.

Preferably $R^8$ is $C_{1-10}$ alkyl, $C_{1-10}$ haloalkyl, aryl($C_{1-6}$)alkyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), arylcarbonyl-($C_{1-6}$)alkyl (wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino and the alkyl group may be optionally substituted by aryl), $C_{2-8}$ alkenyl, $C_{2-8}$ haloalkenyl, aryl($C_{2-6}$)-alkenyl (wherein the aryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), heteroaryl($C_{2-6}$)-alkenyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), $C_{2-6}$ alkynyl, phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{3-7}$ cycloalkyl, $C_{1-6}$ alkoxycarbonyl, $C_{1-6}$ alkylcarbonyl, $C_{1-6}$ haloalkylcarbonyl or aryl($C_{2-6}$)alkenylcarbonyl (wherein the aryl group may be optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), or —C($R^{51}$)($R^{52}$)—[$CR^{53}$=$CR^{54}$]z-$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

More preferably $R^8$ is phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl($C_{2-6}$)alkenyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{2-6}$)alkenyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, or —C($R^{51}$)($R^{52}$)—[$CR^{53}$=$CR^{54}$]z-$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

Most preferably $R^8$ is —C($R^{51}$)($R^{52}$)—[$CR^{53}$=$CR^{54}$]z-$R^{55}$ where z is 1 or 2, preferably 1, $R^{51}$ and $R^{52}$ are each independently H or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

$R^{51}$ and $R^{52}$ are preferably hydrogen.

$R^{53}$ and $R^{54}$ are preferably hydrogen or halogen, especially hydrogen.

$R^{55}$ is preferably phenyl substituted with one to three substituents selected from halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

Preferably each Ra is independently halo, cyano, $C_{1-3}$ alkyl, hydroxy or two Ra groups together with the carbon atom to which they are attached form =O, =S; =NRb, =CRcRd where Rb, Rc and Rd are independently H or optionally substituted alkyl, and p is 0, 1 or 2.

More preferably each Ra is independently fluoro, methyl, hydroxy or two Ra groups together with the carbon atom to which they are attached form a carbonyl group and p is 0, 1 or 2.

Most preferably p is 0.

Certain compounds of formula (I) are novel and as such form a further aspect of the invention. One group of novel compounds are compounds of formula I'

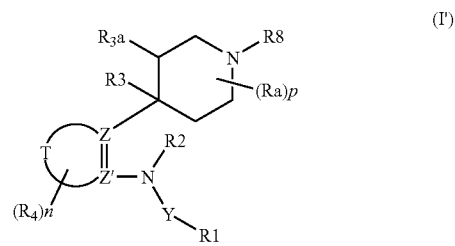

(I')

wherein $R^1$, $R^2$, $R^3$, $R^{3a}$, $R^4$, Ra, T, Y, Z, Z', n and p are as defined in relation to formula I and $R^8$ is —C($R^{51}$)($R^{52}$)—[$CR^{53}$=$CR^{54}$]z-$R^{55}$ where z is 1 or 2, preferably 1, $R^{51}$ and $R^{52}$ are each independently H or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

The compounds in Tables I to XXXI below illustrate the compounds of the invention.

Table I provides 529 compounds of formula Ia

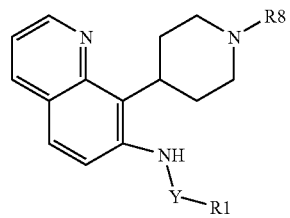

wherein Y is C(=O) and the values of $R^1$ and $R^8$ are given in Table 1.

TABLE 1

| Cmpd No | R⁸ | R¹ |
|---|---|---|
| I-1 | 4-chlorobenzyl | 3-chloro-pyridin-4-yl |
| I-2 | Cinnamyl | 3-chloro-pyridin-4-yl |
| I-3 | 4-chlorocinnamyl | 3-chloro-pyridin-4-yl |
| I-4 | 4-fluorocinnamyl | 3-chloro-pyridin-4-yl |
| I-5 | 4-bromocinnamyl | 3-chloro-pyridin-4-yl |
| I-6 | 4-trifluoromethylcinnamyl | 3-chloro-pyridin-4-yl |
| I-7 | 4-trifluoromethoxycinnamyl | 3-chloro-pyridin-4-yl |
| I-8 | 4-pentafluoroethoxycinnamyl | 3-chloro-pyridin-4-yl |
| I-9 | 4-methoxycinnamyl | 3-chloro-pyridin-4-yl |
| I-10 | 4-ethoxycinnamyl | 3-chloro-pyridin-4-yl |
| I-11 | 4-cyanocinnamyl | 3-chloro-pyridin-4-yl |
| I-12 | 3-(6-chloro-pyridin-3-yl)-allyl | 3-chloro-pyridin-4-yl |
| I-13 | 3-(4-chlorophenyl)-but-2-enyl | 3-chloro-pyridin-4-yl |
| I-14 | 3-(4-chlorophenyl)-3-fluoro-allyl | 3-chloro-pyridin-4-yl |
| I-15 | 3-chloro-4-fluoro-cinnamyl | 3-chloro-pyridin-4-yl |
| I-16 | 3,5-dichloro-cinnamyl | 3-chloro-pyridin-4-yl |
| I-17 | 5-phenyl-penta-2,4-dienyl | 3-chloro-pyridin-4-yl |
| I-18 | 4-isopropyloxycarbonylamino-cinnamyl | 3-chloro-pyridin-4-yl |
| I-19 | 3-naphthalen-2-yl-allyl | 3-chloro-pyridin-4-yl |
| I-20 | 3-(5-trifluoromethyl-pyridin-2-yl)-allyl | 3-chloro-pyridin-4-yl |
| I-21 | 3-(5-chloro-pyridin-2-yl)-allyl | 3-chloro-pyridin-4-yl |
| I-22 | 3-pyridin-4-yl-allyl | 3-chloro-pyridin-4-yl |
| I-23 | 3-(2-Chloro-pyridin-4-yl)-allyl | 3-chloro-pyridin-4-yl |
| I-24 | 4-chlorobenzyl | pyridin-4-yl |
| I-25 | Cinnamyl | pyridin-4-yl |
| I-26 | 4-chlorocinnamyl | pyridin-4-yl |
| I-27 | 4-fluorocinnamyl | pyridin-4-yl |
| I-28 | 4-bromocinnamyl | pyridin-4-yl |
| I-29 | 4-trifluoromethylcinnamyl | pyridin-4-yl |
| I-30 | 4-trifluoromethoxycinnamyl | pyridin-4-yl |
| I-31 | 4-pentafluoroethoxycinnamyl | pyridin-4-yl |
| I-32 | 4-methoxycinnamyl | pyridin-4-yl |
| I-33 | 4-ethoxycinnamyl | pyridin-4-yl |
| I-34 | 4-cyanocinnamyl | pyridin-4-yl |
| I-35 | 3-(6-chloro-pyridin-3-yl)-allyl | pyridin-4-yl |
| I-36 | 3-(4-chlorophenyl)-but-2-enyl | pyridin-4-yl |
| I-37 | 3-(4-chlorophenyl)-3-fluoro-allyl | pyridin-4-yl |
| I-38 | 3-chloro-4-fluoro-cinnamyl | pyridin-4-yl |
| I-39 | 3,5-dichloro-cinnamyl | pyridin-4-yl |
| I-40 | 5-phenyl-penta-2,4-dienyl | pyridin-4-yl |
| I-41 | 4-isopropyloxycarbonylamino-cinnamyl | pyridin-4-yl |
| I-42 | 3-naphthalen-2-yl-allyl | pyridin-4-yl |
| I-43 | 3-(5-trifluoromethyl-pyridin-2-yl)-allyl | pyridin-4-yl |
| I-44 | 3-(5-chloro-pyridin-2-yl)-allyl | pyridin-4-yl |
| I-45 | 3-pyridin-4-yl-allyl | pyridin-4-yl |
| I-46 | 3-(2-Chloro-pyridin-4-yl)-allyl | pyridin-4-yl |
| I-47 | 4-chlorobenzyl | 3,5-dichloro-pyridin-4-yl |
| I-48 | Cinnamyl | 3,5-dichloro-pyridin-4-yl |
| I-49 | 4-chlorocinnamyl | 3,5-dichloro-pyridin-4-yl |
| I-50 | 4-fluorocinnamyl | 3,5-dichloro-pyridin-4-yl |
| I-51 | 4-bromocinnamyl | 3,5-dichloro-pyridin-4-yl |
| I-52 | 4-trifluoromethylcinnamyl | 3,5-dichloro-pyridin-4-yl |
| I-53 | 4-trifluoromethoxycinnamyl | 3,5-dichloro-pyridin-4-yl |
| I-54 | 4-pentafluoroethoxycinnamyl | 3,5-dichloro-pyridin-4-yl |
| I-55 | 4-methoxycinnamyl | 3,5-dichloro-pyridin-4-yl |
| I-56 | 4-ethoxycinnamyl | 3,5-dichloro-pyridin-4-yl |
| I-57 | 4-cyanocinnamyl | 3,5-dichloro-pyridin-4-yl |
| I-58 | 3-(6-chloro-pyridin-3-yl)-allyl | 3,5-dichloro-pyridin-4-yl |
| I-59 | 3-(4-chlorophenyl)-but-2-enyl | 3,5-dichloro-pyridin-4-yl |
| I-60 | 3-(4-chlorophenyl)-3-fluoro-allyl | 3,5-dichloro-pyridin-4-yl |
| I-61 | 3-chloro-4-fluoro-cinnamyl | 3,5-dichloro-pyridin-4-yl |
| I-62 | 3,5-dichloro-cinnamyl | 3,5-dichloro-pyridin-4-yl |
| I-63 | 5-phenyl-penta-2,4-dienyl | 3,5-dichloro-pyridin-4-yl |
| I-64 | 4-isopropyloxycarbonylamino-cinnamyl | 3,5-dichloro-pyridin-4-yl |
| I-65 | 3-naphthalen-2-yl-allyl | 3,5-dichloro-pyridin-4-yl |
| I-66 | 3-(5-trifluoromethyl-pyridin-2-yl)-allyl | 3,5-dichloro-pyridin-4-yl |
| I-67 | 3-(5-chloro-pyridin-2-yl)-allyl | 3,5-dichloro-pyridin-4-yl |
| I-68 | 3-pyridin-4-yl-allyl | 3,5-dichloro-pyridin-4-yl |
| I-69 | 3-(2-Chloro-pyridin-4-yl)-allyl | 3,5-dichloro-pyridin-4-yl |
| I-70 | 4-chlorobenzyl | 3-bromo-pyridin-4-yl |
| I-71 | Cinnamyl | 3-bromo-pyridin-4-yl |
| I-72 | 4-chlorocinnamyl | 3-bromo-pyridin-4-yl |
| I-73 | 4-fluorocinnamyl | 3-bromo-pyridin-4-yl |
| I-74 | 4-bromocinnamyl | 3-bromo-pyridin-4-yl |
| I-75 | 4-trifluoromethylcinnamyl | 3-bromo-pyridin-4-yl |

TABLE 1-continued

| Cmpd No | R⁸ | R¹ |
|---|---|---|
| I-76 | 4-trifluoromethoxycinnamyl | 3-bromo-pyridin-4-yl |
| I-77 | 4-pentafluoroethoxycinnamyl | 3-bromo-pyridin-4-yl |
| I-78 | 4-methoxycinnamyl | 3-bromo-pyridin-4-yl |
| I-79 | 4-ethoxycinnamyl | 3-bromo-pyridin-4-yl |
| I-80 | 4-cyanocinnamyl | 3-bromo-pyridin-4-yl |
| I-81 | 3-(6-chloro-pyridin-3-yl)-allyl | 3-bromo-pyridin-4-yl |
| I-82 | 3-(4-chlorophenyl)-but-2-enyl | 3-bromo-pyridin-4-yl |
| I-83 | 3-(4-chlorophenyl)-3-fluoro-allyl | 3-bromo-pyridin-4-yl |
| I-84 | 3-chloro-4-fluoro-cinnamyl | 3-bromo-pyridin-4-yl |
| I-85 | 3,5-dichloro-cinnamyl | 3-bromo-pyridin-4-yl |
| I-86 | 5-phenyl-penta-2,4-dienyl | 3-bromo-pyridin-4-yl |
| I-87 | 4-isopropyloxycarbonylamino-cinnamyl | 3-bromo-pyridin-4-yl |
| I-88 | 3-naphthalen-2-yl-allyl | 3-bromo-pyridin-4-yl |
| I-89 | 3-(5-trifluoromethyl-pyridin-2-yl)-allyl | 3-bromo-pyridin-4-yl |
| I-90 | 3-(5-chloro-pyridin-2-yl)-allyl | 3-bromo-pyridin-4-yl |
| I-91 | 3-pyridin-4-yl-allyl | 3-bromo-pyridin-4-yl |
| I-92 | 3-(2-Chloro-pyridin-4-yl)-allyl | 3-bromo-pyridin-4-yl |
| I-93 | 4-chlorobenzyl | 3-fluoro-pyridin-4-yl |
| I-94 | Cinnamyl | 3-fluoro-pyridin-4-yl |
| I-95 | 4-chlorocinnamyl | 3-fluoro-pyridin-4-yl |
| I-96 | 4-fluorocinnamyl | 3-fluoro-pyridin-4-yl |
| I-97 | 4-bromocinnamyl | 3-fluoro-pyridin-4-yl |
| I-98 | 4-trifluoromethylcinnamyl | 3-fluoro-pyridin-4-yl |
| I-99 | 4-trifluoromethoxycinnamyl | 3-fluoro-pyridin-4-yl |
| I-100 | 4-pentafluoroethoxycinnamyl | 3-fluoro-pyridin-4-yl |
| I-101 | 4-methoxycinnamyl | 3-fluoro-pyridin-4-yl |
| I-102 | 4-ethoxycinnamyl | 3-fluoro-pyridin-4-yl |
| I-103 | 4-cyanocinnamyl | 3-fluoro-pyridin-4-yl |
| I-104 | 3-(6-chloro-pyridin-3-yl)-allyl | 3-fluoro-pyridin-4-yl |
| I-105 | 3-(4-chlorophenyl)-but-2-enyl | 3-fluoro-pyridin-4-yl |
| I-106 | 3-(4-chlorophenyl)-3-fluoro-allyl | 3-fluoro-pyridin-4-yl |
| I-107 | 3-chloro-4-fluoro-cinnamyl | 3-fluoro-pyridin-4-yl |
| I-108 | 3,5-dichloro-cinnamyl | 3-fluoro-pyridin-4-yl |
| I-109 | 5-phenyl-penta-2,4-dienyl | 3-fluoro-pyridin-4-yl |
| I-110 | 4-isopropyloxycarbonylamino-cinnamyl | 3-fluoro-pyridin-4-yl |
| I-111 | 3-naphthalen-2-yl-allyl | 3-fluoro-pyridin-4-yl |
| I-112 | 3-(5-trifluoromethyl-pyridin-2-yl)-allyl | 3-fluoro-pyridin-4-yl |
| I-113 | 3-(5-chloro-pyridin-2-yl)-allyl | 3-fluoro-pyridin-4-yl |
| I-114 | 3-pyridin-4-yl-allyl | 3-fluoro-pyridin-4-yl |
| I-115 | 3-(2-Chloro-pyridin-4-yl)-allyl | 3-fluoro-pyridin-4-yl |
| I-116 | 4-chlorobenzyl | 3,5-dibromo-pyridin-4-yl |
| I-117 | Cinnamyl | 3,5-dibromo-pyridin-4-yl |
| I-118 | 4-chlorocinnamyl | 3,5-dibromo-pyridin-4-yl |
| I-119 | 4-fluorocinnamyl | 3,5-dibromo-pyridin-4-yl |
| I-120 | 4-bromocinnamyl | 3,5-dibromo-pyridin-4-yl |
| I-121 | 4-trifluoromethylcinnamyl | 3,5-dibromo-pyridin-4-yl |
| I-122 | 4-trifluoromethoxycinnamyl | 3,5-dibromo-pyridin-4-yl |
| I-123 | 4-pentafluoroethoxycinnamyl | 3,5-dibromo-pyridin-4-yl |
| I-124 | 4-methoxycinnamyl | 3,5-dibromo-pyridin-4-yl |
| I-125 | 4-ethoxycinnamyl | 3,5-dibromo-pyridin-4-yl |
| I-126 | 4-cyanocinnamyl | 3,5-dibromo-pyridin-4-yl |
| I-127 | 3-(6-chloro-pyridin-3-yl)-allyl | 3,5-dibromo-pyridin-4-yl |
| I-128 | 3-(4-chlorophenyl)-but-2-enyl | 3,5-dibromo-pyridin-4-yl |
| I-129 | 3-(4-chlorophenyl)-3-fluoro-allyl | 3,5-dibromo-pyridin-4-yl |
| I-130 | 3-chloro-4-fluoro-cinnamyl | 3,5-dibromo-pyridin-4-yl |
| I-131 | 3,5-dichloro-cinnamyl | 3,5-dibromo-pyridin-4-yl |
| I-132 | 5-phenyl-penta-2,4-dienyl | 3,5-dibromo-pyridin-4-yl |
| I-133 | 4-isopropyloxycarbonylamino-cinnamyl | 3,5-dibromo-pyridin-4-yl |
| I-134 | 3-naphthalen-2-yl-allyl | 3,5-dibromo-pyridin-4-yl |
| I-135 | 3-(5-trifluoromethyl-pyridin-2-yl)-allyl | 3,5-dibromo-pyridin-4-yl |
| I-136 | 3-(5-chloro-pyridin-2-yl)-allyl | 3,5-dibromo-pyridin-4-yl |
| I-137 | 3-pyridin-4-yl-allyl | 3,5-dibromo-pyridin-4-yl |
| I-138 | 3-(2-Chloro-pyridin-4-yl)-allyl | 3,5-dibromo-pyridin-4-yl |
| I-139 | 4-chlorobenzyl | 3-trifluoromethyl-pyridin-4-yl |
| I-140 | Cinnamyl | 3-trifluoromethyl-pyridin-4-yl |
| I-141 | 4-chlorocinnamyl | 3-trifluoromethyl-pyridin-4-yl |
| I-142 | 4-fluorocinnamyl | 3-trifluoromethyl-pyridin-4-yl |
| I-143 | 4-bromocinnamyl | 3-trifluoromethyl-pyridin-4-yl |
| I-144 | 4-trifluoromethylcinnamyl | 3-trifluoromethyl-pyridin-4-yl |
| I-145 | 4-trifluoromethoxycinnamyl | 3-trifluoromethyl-pyridin-4-yl |
| I-146 | 4-pentafluoroethoxycinnamyl | 3-trifluoromethyl-pyridin-4-yl |
| I-147 | 4-methoxycinnamyl | 3-trifluoromethyl-pyridin-4-yl |
| I-148 | 4-ethoxycinnamyl | 3-trifluoromethyl-pyridin-4-yl |
| I-149 | 4-cyanocinnamyl | 3-trifluoromethyl-pyridin-4-yl |
| I-150 | 3-(6-chloro-pyridin-3-yl)-allyl | 3-trifluoromethyl-pyridin-4-yl |

TABLE 1-continued

| Cmpd No | R⁸ | R¹ |
|---|---|---|
| I-151 | 3-(4-chlorophenyl)-but-2-enyl | 3-trifluoromethyl-pyridin-4-yl |
| I-152 | 3-(4-chlorophenyl)-3-fluoro-allyl | 3-trifluoromethyl-pyridin-4-yl |
| I-153 | 3-chloro-4-fluoro-cinnamyl | 3-trifluoromethyl-pyridin-4-yl |
| I-154 | 3,5-dichloro-cinnamyl | 3-trifluoromethyl-pyridin-4-yl |
| I-155 | 5-phenyl-penta-2,4-dienyl | 3-trifluoromethyl-pyridin-4-yl |
| I-156 | 4-isopropyloxycarbonylamino-cinnamyl | 3-trifluoromethyl-pyridin-4-yl |
| I-157 | 3-naphthalen-2-yl-allyl | 3-trifluoromethyl-pyridin-4-yl |
| I-158 | 3-(5-trifluoromethyl-pyridin-2-yl)-allyl | 3-trifluoromethyl-pyridin-4-yl |
| I-159 | 3-(5-chloro-pyridin-2-yl)-allyl | 3-trifluoromethyl-pyridin-4-yl |
| I-160 | 3-pyridin-4-yl-allyl | 3-trifluoromethyl-pyridin-4-yl |
| I-161 | 3-(2-Chloro-pyridin-4-yl)-allyl | 3-trifluoromethyl-pyridin-4-yl |
| I-162 | 4-chlorobenzyl | 3,5-difluoro-pyridin-4-yl |
| I-163 | Cinnamyl | 3,5-difluoro-pyridin-4-yl |
| I-164 | 4-chlorocinnamyl | 3,5-difluoro-pyridin-4-yl |
| I-165 | 4-fluorocinnamyl | 3,5-difluoro-pyridin-4-yl |
| I-166 | 4-bromocinnamyl | 3,5-difluoro-pyridin-4-yl |
| I-167 | 4-trifluoromethylcinnamyl | 3,5-difluoro-pyridin-4-yl |
| I-168 | 4-trifluoromethoxycinnamyl | 3,5-difluoro-pyridin-4-yl |
| I-169 | 4-pentafluoroethoxycinnamyl | 3,5-difluoro-pyridin-4-yl |
| I-170 | 4-methoxycinnamyl | 3,5-difluoro-pyridin-4-yl |
| I-171 | 4-ethoxycinnamyl | 3,5-difluoro-pyridin-4-yl |
| I-172 | 4-cyanocinnamyl | 3,5-difluoro-pyridin-4-yl |
| I-173 | 3-(6-chloro-pyridin-3-yl)-allyl | 3,5-difluoro-pyridin-4-yl |
| I-174 | 3-(4-chlorophenyl)-but-2-enyl | 3,5-difluoro-pyridin-4-yl |
| I-175 | 3-(4-chlorophenyl)-3-fluoro-allyl | 3,5-difluoro-pyridin-4-yl |
| I-176 | 3-chloro-4-fluoro-cinnamyl | 3,5-difluoro-pyridin-4-yl |
| I-177 | 3,5-dichloro-cinnamyl | 3,5-difluoro-pyridin-4-yl |
| I-178 | 5-phenyl-penta-2,4-dienyl | 3,5-difluoro-pyridin-4-yl |
| I-179 | 4-isopropyloxycarbonylamino-cinnamyl | 3,5-difluoro-pyridin-4-yl |
| I-180 | 3-naphthalen-2-yl-allyl | 3,5-difluoro-pyridin-4-yl |
| I-181 | 3-(5-trifluoromethyl-pyridin-2-yl)-allyl | 3,5-difluoro-pyridin-4-yl |
| I-182 | 3-(5-chloro-pyridin-2-yl)-allyl | 3,5-difluoro-pyridin-4-yl |
| I-183 | 3-pyridin-4-yl-allyl | 3,5-difluoro-pyridin-4-yl |
| I-184 | 3-(2-Chloro-pyridin-4-yl)-allyl | 3,5-difluoro-pyridin-4-yl |
| I-185 | 4-chlorobenzyl | Methyl |
| I-186 | Cinnamyl | Methyl |
| I-187 | 4-chlorocinnamyl | Methyl |
| I-188 | 4-fluorocinnamyl | Methyl |
| I-189 | 4-bromocinnamyl | Methyl |
| I-190 | 4-trifluoromethylcinnamyl | Methyl |
| I-191 | 4-trifluoromethoxycinnamyl | Methyl |
| I-192 | 4-pentafluoroethoxycinnamyl | Methyl |
| I-193 | 4-methoxycinnamyl | Methyl |
| I-194 | 4-ethoxycinnamyl | Methyl |
| I-195 | 4-cyanocinnamyl | Methyl |
| I-196 | 3-(6-chloro-pyridin-3-yl)-allyl | Methyl |
| I-197 | 3-(4-chlorophenyl)-but-2-enyl | Methyl |
| I-198 | 3-(4-chlorophenyl)-3-fluoro-allyl | Methyl |
| I-199 | 3-chloro-4-fluoro-cinnamyl | Methyl |
| I-200 | 3,5-dichloro-cinnamyl | Methyl |
| I-201 | 5-phenyl-penta-2,4-dienyl | Methyl |
| I-202 | 4-isopropyloxycarbonylamino-cinnamyl | Methyl |
| I-203 | 3-naphthalen-2-yl-allyl | Methyl |
| I-204 | 3-(5-trifluoromethyl-pyridin-2-yl)-allyl | Methyl |
| I-205 | 3-(5-chloro-pyridin-2-yl)-allyl | Methyl |
| I-206 | 3-pyridin-4-yl-allyl | Methyl |
| I-207 | 3-(2-Chloro-pyridin-4-yl)-allyl | Methyl |
| I-208 | 4-chlorobenzyl | 2-methoxy-ethyl |
| I-209 | Cinnamyl | 2-methoxy-ethyl |
| I-210 | 4-chlorocinnamyl | 2-methoxy-ethyl |
| I-211 | 4-fluorocinnamyl | 2-methoxy-ethyl |
| I-212 | 4-bromocinnamyl | 2-methoxy-ethyl |
| I-213 | 4-trifluoromethylcinnamyl | 2-methoxy-ethyl |
| I-214 | 4-trifluoromethoxycinnamyl | 2-methoxy-ethyl |
| I-215 | 4-pentafluoroethoxycinnamyl | 2-methoxy-ethyl |
| I-216 | 4-methoxycinnamyl | 2-methoxy-ethyl |
| I-217 | 4-ethoxycinnamyl | 2-methoxy-ethyl |
| I-218 | 4-cyanocinnamyl | 2-methoxy-ethyl |
| I-219 | 3-(6-chloro-pyridin-3-yl)-allyl | 2-methoxy-ethyl |
| I-220 | 3-(4-chlorophenyl)-but-2-enyl | 2-methoxy-ethyl |
| I-221 | 3-(4-chlorophenyl)-3-fluoro-allyl | 2-methoxy-ethyl |
| I-222 | 3-chloro-4-fluoro-cinnamyl | 2-methoxy-ethyl |
| I-223 | 3,5-dichloro-cinnamyl | 2-methoxy-ethyl |
| I-224 | 5-phenyl-penta-2,4-dienyl | 2-methoxy-ethyl |

TABLE 1-continued

| Cmpd No | R⁸ | R¹ |
|---|---|---|
| I-225 | 4-isopropyloxycarbonylamino-cinnamyl | 2-methoxy-ethyl |
| I-226 | 3-naphthalen-2-yl-allyl | 2-methoxy-ethyl |
| I-227 | 3-(5-trifluoromethyl-pyridin-2-yl)-allyl | 2-methoxy-ethyl |
| I-228 | 3-(5-chloro-pyridin-2-yl)-allyl | 2-methoxy-ethyl |
| I-229 | 3-pyridin-4-yl-allyl | 2-methoxy-ethyl |
| I-230 | 3-(2-Chloro-pyridin-4-yl)-allyl | 2-methoxy-ethyl |
| I-231 | 4-chlorobenzyl | 2,2,2-trifluoroethyl |
| I-232 | Cinnamyl | 2,2,2-trifluoroethyl |
| I-233 | 4-chlorocinnamyl | 2,2,2-trifluoroethyl |
| I-234 | 4-fluorocinnamyl | 2,2,2-trifluoroethyl |
| I-235 | 4-bromocinnamyl | 2,2,2-trifluoroethyl |
| I-236 | 4-trifluoromethylcinnamyl | 2,2,2-trifluoroethyl |
| I-237 | 4-trifluoromethoxycinnamyl | 2,2,2-trifluoroethyl |
| I-238 | 4-pentafluoroethoxycinnamyl | 2,2,2-trifluoroethyl |
| I-239 | 4-methoxycinnamyl | 2,2,2-trifluoroethyl |
| I-240 | 4-ethoxycinnamyl | 2,2,2-trifluoroethyl |
| I-241 | 4-cyanocinnamyl | 2,2,2-trifluoroethyl |
| I-242 | 3-(6-chloro-pyridin-3-yl)-allyl | 2,2,2-trifluoroethyl |
| I-243 | 3-(4-chlorophenyl)-but-2-enyl | 2,2,2-trifluoroethyl |
| I-244 | 3-(4-chlorophenyl)-3-fluoro-allyl | 2,2,2-trifluoroethyl |
| I-245 | 3-chloro-4-fluoro-cinnamyl | 2,2,2-trifluoroethyl |
| I-246 | 3,5-dichloro-cinnamyl | 2,2,2-trifluoroethyl |
| I-247 | 5-phenyl-penta-2,4-dienyl | 2,2,2-trifluoroethyl |
| I-248 | 4-isopropyloxycarbonylamino-cinnamyl | 2,2,2-trifluoroethyl |
| I-249 | 3-naphthalen-2-yl-allyl | 2,2,2-trifluoroethyl |
| I-250 | 3-(5-trifluoromethyl-pyridin-2-yl)-allyl | 2,2,2-trifluoroethyl |
| I-251 | 3-(5-chloro-pyridin-2-yl)-allyl | 2,2,2-trifluoroethyl |
| I-252 | 3-pyridin-4-yl-allyl | 2,2,2-trifluoroethyl |
| I-253 | 3-(2-Chloro-pyridin-4-yl)-allyl | 2,2,2-trifluoroethyl |
| I-254 | 4-chlorobenzyl | Methoxy |
| I-255 | Cinnamyl | Methoxy |
| I-256 | 4-chlorocinnamyl | Methoxy |
| I-257 | 4-fluorocinnamyl | Methoxy |
| I-258 | 4-bromocinnamyl | Methoxy |
| I-259 | 4-trifluoromethylcinnamyl | Methoxy |
| I-260 | 4-trifluoromethoxycinnamyl | Methoxy |
| I-261 | 4-pentafluoroethoxycinnamyl | Methoxy |
| I-262 | 4-methoxycinnamyl | Methoxy |
| I-263 | 4-ethoxycinnamyl | Methoxy |
| I-264 | 4-cyanocinnamyl | Methoxy |
| I-265 | 3-(6-chloro-pyridin-3-yl)-allyl | Methoxy |
| I-266 | 3-(4-chlorophenyl)-but-2-enyl | Methoxy |
| I-267 | 3-(4-chlorophenyl)-3-fluoro-allyl | Methoxy |
| I-268 | 3-chloro-4-fluoro-cinnamyl | Methoxy |
| I-269 | 3,5-dichloro-cinnamyl | Methoxy |
| I-270 | 5-phenyl-penta-2,4-dienyl | Methoxy |
| I-271 | 4-isopropyloxycarbonylamino-cinnamyl | Methoxy |
| I-272 | 3-naphthalen-2-yl-allyl | Methoxy |
| I-273 | 3-(5-trifluoromethyl-pyridin-2-yl)-allyl | Methoxy |
| I-274 | 3-(5-chloro-pyridin-2-yl)-allyl | Methoxy |
| I-275 | 3-pyridin-4-yl-allyl | Methoxy |
| I-276 | 3-(2-Chloro-pyridin-4-yl)-allyl | Methoxy |
| I-277 | 4-chlorobenzyl | 2,1,3-benzoxadiazol-5-yl |
| I-278 | Cinnamyl | 2,1,3-benzoxadiazol-5-yl |
| I-279 | 4-chlorocinnamyl | 2,1,3-benzoxadiazol-5-yl |
| I-280 | 4-fluorocinnamyl | 2,1,3-benzoxadiazol-5-yl |
| I-281 | 4-bromocinnamyl | 2,1,3-benzoxadiazol-5-yl |
| I-282 | 4-trifluoromethylcinnamyl | 2,1,3-benzoxadiazol-5-yl |
| I-283 | 4-trifluoromethoxycinnamyl | 2,1,3-benzoxadiazol-5-yl |
| I-284 | 4-pentafluoroethoxycinnamyl | 2,1,3-benzoxadiazol-5-yl |
| I-285 | 4-methoxycinnamyl | 2,1,3-benzoxadiazol-5-yl |
| I-286 | 4-ethoxycinnamyl | 2,1,3-benzoxadiazol-5-yl |
| I-287 | 4-cyanocinnamyl | 2,1,3-benzoxadiazol-5-yl |
| I-288 | 3-(6-chloro-pyridin-3-yl)-allyl | 2,1,3-benzoxadiazol-5-yl |
| I-289 | 3-(4-chlorophenyl)-but-2-enyl | 2,1,3-benzoxadiazol-5-yl |
| I-290 | 3-(4-chlorophenyl)-3-fluoro-allyl | 2,1,3-benzoxadiazol-5-yl |
| I-291 | 3-chloro-4-fluoro-cinnamyl | 2,1,3-benzoxadiazol-5-yl |
| I-292 | 3,5-dichloro-cinnamyl | 2,1,3-benzoxadiazol-5-yl |
| I-293 | 5-phenyl-penta-2,4-dienyl | 2,1,3-benzoxadiazol-5-yl |
| I-294 | 4-isopropyloxycarbonylamino-cinnamyl | 2,1,3-benzoxadiazol-5-yl |
| I-295 | 3-naphthalen-2-yl-allyl | 2,1,3-benzoxadiazol-5-yl |
| I-296 | 3-(5-trifluoromethyl-pyridin-2-yl)-allyl | 2,1,3-benzoxadiazol-5-yl |
| I-297 | 3-(5-chloro-pyridin-2-yl)-allyl | 2,1,3-benzoxadiazol-5-yl |
| I-298 | 3-pyridin-4-yl-allyl | 2,1,3-benzoxadiazol-5-yl |

TABLE 1-continued

| Cmpd No | R⁸ | R¹ |
|---|---|---|
| I-299 | 3-(2-Chloro-pyridin-4-yl)-allyl | 2,1,3-benzoxadiazol-5-yl |
| I-300 | 4-chlorobenzyl | 3-methoxypropylamino |
| I-301 | Cinnamyl | 3-methoxypropylamino |
| I-302 | 4-chlorocinnamyl | 3-methoxypropylamino |
| I-303 | 4-fluorocinnamyl | 3-methoxypropylamino |
| I-304 | 4-bromocinnamyl | 3-methoxypropylamino |
| I-305 | 4-trifluoromethylcinnamyl | 3-methoxypropylamino |
| I-306 | 4-trifluoromethoxycinnamyl | 3-methoxypropylamino |
| I-307 | 4-pentafluoroethoxycinnamyl | 3-methoxypropylamino |
| I-308 | 4-methoxycinnamyl | 3-methoxypropylamino |
| I-309 | 4-ethoxycinnamyl | 3-methoxypropylamino |
| I-310 | 4-cyanocinnamyl | 3-methoxypropylamino |
| I-311 | 3-(6-chloro-pyridin-3-yl)-allyl | 3-methoxypropylamino |
| I-312 | 3-(4-chlorophenyl)-but-2-enyl | 3-methoxypropylamino |
| I-313 | 3-(4-chlorophenyl)-3-fluoro-allyl | 3-methoxypropylamino |
| I-314 | 3-chloro-4-fluoro-cinnamyl | 3-methoxypropylamino |
| I-315 | 3,5-dichloro-cinnamyl | 3-methoxypropylamino |
| I-316 | 5-phenyl-penta-2,4-dienyl | 3-methoxypropylamino |
| I-317 | 4-isopropyloxycarbonylamino-cinnamyl | 3-methoxypropylamino |
| I-318 | 3-naphthalen-2-yl-allyl | 3-methoxypropylamino |
| I-319 | 3-(5-trifluoromethyl-pyridin-2-yl)-allyl | 3-methoxypropylamino |
| I-320 | 3-(5-chloro-pyridin-2-yl)-allyl | 3-methoxypropylamino |
| I-321 | 3-pyridin-4-yl-allyl | 3-methoxypropylamino |
| I-322 | 3-(2-Chloro-pyridin-4-yl)-allyl | 3-methoxypropylamino |
| I-323 | 4-chlorobenzyl | 2-chloro-thiazol-5-ylmethylamino |
| I-324 | Cinnamyl | 2-chloro-thiazol-5-ylmethylamino |
| I-325 | 4-chlorocinnamyl | 2-chloro-thiazol-5-ylmethylamino |
| I-326 | 4-fluorocinnamyl | 2-chloro-thiazol-5-ylmethylamino |
| I-327 | 4-bromocinnamyl | 2-chloro-thiazol-5-ylmethylamino |
| I-328 | 4-trifluoromethylcinnamyl | 2-chloro-thiazol-5-ylmethylamino |
| I-329 | 4-trifluoromethoxycinnamyl | 2-chloro-thiazol-5-ylmethylamino |
| I-330 | 4-pentafluoroethoxycinnamyl | 2-chloro-thiazol-5-ylmethylamino |
| I-331 | 4-methoxycinnamyl | 2-chloro-thiazol-5-ylmethylamino |
| I-332 | 4-ethoxycinnamyl | 2-chloro-thiazol-5-ylmethylamino |
| I-333 | 4-cyanocinnamyl | 2-chloro-thiazol-5-ylmethylamino |
| I-334 | 3-(6-chloro-pyridin-3-yl)-allyl | 2-chloro-thiazol-5-ylmethylamino |
| I-335 | 3-(4-chlorophenyl)-but-2-enyl | 2-chloro-thiazol-5-ylmethylamino |
| I-336 | 3-(4-chlorophenyl)-3-fluoro-allyl | 2-chloro-thiazol-5-ylmethylamino |
| I-337 | 3-chloro-4-fluoro-cinnamyl | 2-chloro-thiazol-5-ylmethylamino |
| I-338 | 3,5-dichloro-cinnamyl | 2-chloro-thiazol-5-ylmethylamino |
| I-339 | 5-phenyl-penta-2,4-dienyl | 2-chloro-thiazol-5-ylmethylamino |
| I-340 | 4-isopropyloxycarbonylamino-cinnamyl | 2-chloro-thiazol-5-ylmethylamino |
| I-341 | 3-naphthalen-2-yl-allyl | 2-chloro-thiazol-5-ylmethylamino |
| I-342 | 3-(5-trifluoromethyl-pyridin-2-yl)-allyl | 2-chloro-thiazol-5-ylmethylamino |
| I-343 | 3-(5-chloro-pyridin-2-yl)-allyl | 2-chloro-thiazol-5-ylmethylamino |
| I-344 | 3-pyridin-4-yl-allyl | 2-chloro-thiazol-5-ylmethylamino |
| I-345 | 3-(2-Chloro-pyridin-4-yl)-allyl | 2-chloro-thiazol-5-ylmethylamino |
| I-346 | 4-chlorobenzyl | i-propylamino |
| I-347 | Cinnamyl | i-propylamino |
| I-348 | 4-chlorocinnamyl | i-propylamino |
| I-349 | 4-fluorocinnamyl | i-propylamino |
| I-350 | 4-bromocinnamyl | i-propylamino |
| I-351 | 4-trifluoromethylcinnamyl | i-propylamino |
| I-352 | 4-trifluoromethoxycinnamyl | i-propylamino |
| I-353 | 4-pentafluoroethoxycinnamyl | i-propylamino |
| I-354 | 4-methoxycinnamyl | i-propylamino |
| I-355 | 4-ethoxycinnamyl | i-propylamino |
| I-356 | 4-cyanocinnamyl | i-propylamino |
| I-357 | 3-(6-chloro-pyridin-3-yl)-allyl | i-propylamino |
| I-358 | 3-(4-chlorophenyl)-but-2-enyl | i-propylamino |
| I-359 | 3-(4-chlorophenyl)-3-fluoro-allyl | i-propylamino |
| I-360 | 3-chloro-4-fluoro-cinnamyl | i-propylamino |
| I-361 | 3,5-dichloro-cinnamyl | i-propylamino |
| I-362 | 5-phenyl-penta-2,4-dienyl | i-propylamino |
| I-363 | 4-isopropyloxycarbonylamino-cinnamyl | i-propylamino |
| I-364 | 3-naphthalen-2-yl-allyl | i-propylamino |
| I-365 | 3-(5-trifluoromethyl-pyridin-2-yl)-allyl | i-propylamino |
| I-366 | 3-(5-chloro-pyridin-2-yl)-allyl | i-propylamino |
| I-367 | 3-pyridin-4-yl-allyl | i-propylamino |
| I-368 | 3-(2-Chloro-pyridin-4-yl)-allyl | i-propylamino |
| I-369 | 4-chlorobenzyl | 2-(1,3-dioxolan-2-yl)ethylamino |
| I-370 | Cinnamyl | 2-(1,3-dioxolan-2-yl)ethylamino |
| I-371 | 4-chlorocinnamyl | 2-(1,3-dioxolan-2-yl)ethylamino |
| I-372 | 4-fluorocinnamyl | 2-(1,3-dioxolan-2-yl)ethylamino |
| I-373 | 4-bromocinnamyl | 2-(1,3-dioxolan-2-yl)ethylamino |

TABLE 1-continued

| Cmpd No | R⁸ | R¹ |
| --- | --- | --- |
| I-374 | 4-trifluoromethylcinnamyl | 2-(1,3-dioxolan-2-yl)ethylamino |
| I-375 | 4-trifluoromethoxycinnamyl | 2-(1,3-dioxolan-2-yl)ethylamino |
| I-376 | 4-pentafluoroethoxycinnamyl | 2-(1,3-dioxolan-2-yl)ethylamino |
| I-377 | 4-methoxycinnamyl | 2-(1,3-dioxolan-2-yl)ethylamino |
| I-378 | 4-ethoxycinnamyl | 2-(1,3-dioxolan-2-yl)ethylamino |
| I-379 | 4-cyanocinnamyl | 2-(1,3-dioxolan-2-yl)ethylamino |
| I-380 | 3-(6-chloro-pyridin-3-yl)-allyl | 2-(1,3-dioxolan-2-yl)ethylamino |
| I-381 | 3-(4-chlorophenyl)-but-2-enyl | 2-(1,3-dioxolan-2-yl)ethylamino |
| I-382 | 3-(4-chlorophenyl)-3-fluoro-allyl | 2-(1,3-dioxolan-2-yl)ethylamino |
| I-383 | 3-chloro-4-fluoro-cinnamyl | 2-(1,3-dioxolan-2-yl)ethylamino |
| I-384 | 3,5-dichloro-cinnamyl | 2-(1,3-dioxolan-2-yl)ethylamino |
| I-385 | 5-phenyl-penta-2,4-dienyl | 2-(1,3-dioxolan-2-yl)ethylamino |
| I-386 | 4-isopropyloxycarbonylamino-cinnamyl | 2-(1,3-dioxolan-2-yl)ethylamino |
| I-387 | 3-naphthalen-2-yl-allyl | 2-(1,3-dioxolan-2-yl)ethylamino |
| I-388 | 3-(5-trifluoromethyl-pyridin-2-yl)-allyl | 2-(1,3-dioxolan-2-yl)ethylamino |
| I-389 | 3-(5-chloro-pyridin-2-yl)-allyl | 2-(1,3-dioxolan-2-yl)ethylamino |
| I-390 | 3-pyridin-4-yl-allyl | 2-(1,3-dioxolan-2-yl)ethylamino |
| I-391 | 3-(2-Chloro-pyridin-4-yl)-allyl | 2-(1,3-dioxolan-2-yl)ethylamino |
| I-392 | 4-chlorobenzyl | 3-chloro-pyridin-4-yl-methylamino |
| I-393 | Cinnamyl | 3-chloro-pyridin-4-yl-methylamino |
| I-394 | 4-chlorocinnamyl | 3-chloro-pyridin-4-yl-methylamino |
| I-395 | 4-fluorocinnamyl | 3-chloro-pyridin-4-yl-methylamino |
| I-396 | 4-bromocinnamyl | 3-chloro-pyridin-4-yl-methylamino |
| I-397 | 4-trifluoromethylcinnamyl | 3-chloro-pyridin-4-yl-methylamino |
| I-398 | 4-trifluoromethoxycinnamyl | 3-chloro-pyridin-4-yl-methylamino |
| I-399 | 4-pentafluoroethoxycinnamyl | 3-chloro-pyridin-4-yl-methylamino |
| I-400 | 4-methoxycinnamyl | 3-chloro-pyridin-4-yl-methylamino |
| I-401 | 4-ethoxycinnamyl | 3-chloro-pyridin-4-yl-methylamino |
| I-402 | 4-cyanocinnamyl | 3-chloro-pyridin-4-yl-methylamino |
| I-403 | 3-(6-chloro-pyridin-3-yl)-allyl | 3-chloro-pyridin-4-yl-methylamino |
| I-404 | 3-(4-chlorophenyl)-but-2-enyl | 3-chloro-pyridin-4-yl-methylamino |
| I-405 | 3-(4-chlorophenyl)-3-fluoro-allyl | 3-chloro-pyridin-4-yl-methylamino |
| I-406 | 3-chloro-4-fluoro-cinnamyl | 3-chloro-pyridin-4-yl-methylamino |
| I-407 | 3,5-dichloro-cinnamyl | 3-chloro-pyridin-4-yl-methylamino |
| I-408 | 5-phenyl-penta-2,4-dienyl | 3-chloro-pyridin-4-yl-methylamino |
| I-409 | 4-isopropyloxycarbonylamino-cinnamyl | 3-chloro-pyridin-4-yl-methylamino |
| I-410 | 3-naphthalen-2-yl-allyl | 3-chloro-pyridin-4-yl-methylamino |
| I-411 | 3-(5-trifluoromethyl-pyridin-2-yl)-allyl | 3-chloro-pyridin-4-yl-methylamino |
| I-412 | 3-(5-chloro-pyridin-2-yl)-allyl | 3-chloro-pyridin-4-yl-methylamino |
| I-413 | 3-pyridin-4-yl-allyl | 3-chloro-pyridin-4-yl-methylamino |
| I-414 | 3-(2-Chloro-pyridin-4-yl)-allyl | 3-chloro-pyridin-4-yl-methylamino |
| I-415 | 4-chlorobenzyl | 4-trifluoromethyl-pyridin-3-yl-methylamino |
| I-416 | Cinnamyl | 4-trifluoromethyl-pyridin-3-yl-methylamino |
| I-417 | 4-chlorocinnamyl | 4-trifluoromethyl-pyridin-3-yl-methylamino |
| I-418 | 4-fluorocinnamyl | 4-trifluoromethyl-pyridin-3-yl-methylamino |
| I-419 | 4-bromocinnamyl | 4-trifluoromethyl-pyridin-3-yl-methylamino |
| I-420 | 4-trifluoromethylcinnamyl | 4-trifluoromethyl-pyridin-3-yl-methylamino |
| I-421 | 4-trifluoromethoxycinnamyl | 4-trifluoromethyl-pyridin-3-yl-methylamino |
| I-422 | 4-pentafluoroethoxycinnamyl | 4-trifluoromethyl-pyridin-3-yl-methylamino |
| I-423 | 4-methoxycinnamyl | 4-trifluoromethyl-pyridin-3-yl-methylamino |
| I-424 | 4-ethoxycinnamyl | 4-trifluoromethyl-pyridin-3-yl-methylamino |
| I-425 | 4-cyanocinnamyl | 4-trifluoromethyl-pyridin-3-yl-methylamino |
| I-426 | 3-(6-chloro-pyridin-3-yl)-allyl | 4-trifluoromethyl-pyridin-3-yl-methylamino |
| I-427 | 3-(4-chlorophenyl)-but-2-enyl | 4-trifluoromethyl-pyridin-3-yl-methylamino |
| I-428 | 3-(4-chlorophenyl)-3-fluoro-allyl | 4-trifluoromethyl-pyridin-3-yl-methylamino |
| I-429 | 3-chloro-4-fluoro-cinnamyl | 4-trifluoromethyl-pyridin-3-yl-methylamino |
| I-430 | 3,5-dichloro-cinnamyl | 4-trifluoromethyl-pyridin-3-yl-methylamino |
| I-431 | 5-phenyl-penta-2,4-dienyl | 4-trifluoromethyl-pyridin-3-yl-methylamino |

TABLE 1-continued

| Cmpd No | R⁸ | R¹ |
|---|---|---|
| I-432 | 4-isopropyloxycarbonylamino-cinnamyl | 4-trifluoromethyl-pyridin-3-yl-methylamino |
| I-433 | 3-naphthalen-2-yl-allyl | 4-trifluoromethyl-pyridin-3-yl-methylamino |
| I-434 | 3-(5-trifluoromethyl-pyridin-2-yl)-allyl | 4-trifluoromethyl-pyridin-3-yl-methylamino |
| I-435 | 3-(5-chloro-pyridin-2-yl)-allyl | 4-trifluoromethyl-pyridin-3-yl-methylamino |
| I-436 | 3-pyridin-4-yl-allyl | 4-trifluoromethyl-pyridin-3-yl-methylamino |
| I-437 | 3-(2-Chloro-pyridin-4-yl)-allyl | 4-trifluoromethyl-pyridin-3-yl-methylamino |
| I-438 | 4-chlorobenzyl | Methylamino |
| I-439 | Cinnamyl | Methylamino |
| I-440 | 4-chlorocinnamyl | Methylamino |
| I-441 | 4-fluorocinnamyl | Methylamino |
| I-442 | 4-bromocinnamyl | Methylamino |
| I-443 | 4-trifluoromethylcinnamyl | Methylamino |
| I-444 | 4-trifluoromethoxycinnamyl | Methylamino |
| I-445 | 4-pentafluoroethoxycinnamyl | Methylamino |
| I-446 | 4-methoxycinnamyl | Methylamino |
| I-447 | 4-ethoxycinnamyl | Methylamino |
| I-448 | 4-cyanocinnamyl | Methylamino |
| I-449 | 3-(6-chloro-pyridin-3-yl)-allyl | Methylamino |
| I-450 | 3-(4-chlorophenyl)-but-2-enyl | Methylamino |
| I-451 | 3-(4-chlorophenyl)-3-fluoro-allyl | Methylamino |
| I-452 | 3-chloro-4-fluoro-cinnamyl | Methylamino |
| I-453 | 3,5-dichloro-cinnamyl | Methylamino |
| I-454 | 5-phenyl-penta-2,4-dienyl | Methylamino |
| I-455 | 4-isopropyloxycarbonylamino-cinnamyl | Methylamino |
| I-456 | 3-naphthalen-2-yl-allyl | Methylamino |
| I-457 | 3-(5-trifluoromethyl-pyridin-2-yl)-allyl | Methylamino |
| I-458 | 3-(5-chloro-pyridin-2-yl)-allyl | Methylamino |
| I-459 | 3-pyridin-4-yl-allyl | Methylamino |
| I-460 | 3-(2-Chloro-pyridin-4-yl)-allyl | Methylamino |
| I-461 | 4-chlorobenzyl | Ethylamino |
| I-462 | Cinnamyl | Ethylamino |
| I-463 | 4-chlorocinnamyl | Ethylamino |
| I-464 | 4-fluorocinnamyl | Ethylamino |
| I-465 | 4-bromocinnamyl | Ethylamino |
| I-466 | 4-trifluoromethylcinnamyl | Ethylamino |
| I-467 | 4-trifluoromethoxycinnamyl | Ethylamino |
| I-468 | 4-pentafluoroethoxycinnamyl | Ethylamino |
| I-469 | 4-methoxycinnamyl | Ethylamino |
| I-470 | 4-ethoxycinnamyl | Ethylamino |
| I-471 | 4-cyanocinnamyl | Ethylamino |
| I-472 | 3-(6-chloro-pyridin-3-yl)-allyl | Ethylamino |
| I-473 | 3-(4-chlorophenyl)-but-2-enyl | Ethylamino |
| I-474 | 3-(4-chlorophenyl)-3-fluoro-allyl | Ethylamino |
| I-475 | 3-chloro-4-fluoro-cinnamyl | Ethylamino |
| I-476 | 3,5-dichloro-cinnamyl | Ethylamino |
| I-477 | 5-phenyl-penta-2,4-dienyl | Ethylamino |
| I-478 | 4-isopropyloxycarbonylamino-cinnamyl | Ethylamino |
| I-479 | 3-naphthalen-2-yl-allyl | Ethylamino |
| I-480 | 3-(5-trifluoromethyl-pyridin-2-yl)-allyl | Ethylamino |
| I-481 | 3-(5-chloro-pyridin-2-yl)-allyl | Ethylamino |
| I-482 | 3-pyridin-4-yl-allyl | Ethylamino |
| I-483 | 3-(2-Chloro-pyridin-4-yl)-allyl | Ethylamino |
| I-484 | 4-chlorobenzyl | 3-chloro-pyridin-4-yl-amino |
| I-485 | Cinnamyl | 3-chloro-pyridin-4-yl-amino |
| I-486 | 4-chlorocinnamyl | 3-chloro-pyridin-4-yl-amino |
| I-487 | 4-fluorocinnamyl | 3-chloro-pyridin-4-yl-amino |
| I-488 | 4-bromocinnamyl | 3-chloro-pyridin-4-yl-amino |
| I-489 | 4-trifluoromethylcinnamyl | 3-chloro-pyridin-4-yl-amino |
| I-490 | 4-trifluoromethoxycinnamyl | 3-chloro-pyridin-4-yl-amino |
| I-491 | 4-pentafluoroethoxycinnamyl | 3-chloro-pyridin-4-yl-amino |
| I-492 | 4-methoxycinnamyl | 3-chloro-pyridin-4-yl-amino |
| I-493 | 4-ethoxycinnamyl | 3-chloro-pyridin-4-yl-amino |
| I-494 | 4-cyanocinnamyl | 3-chloro-pyridin-4-yl-amino |
| I-495 | 3-(6-chloro-pyridin-3-yl)-allyl | 3-chloro-pyridin-4-yl-amino |
| I-496 | 3-(4-chlorophenyl)-but-2-enyl | 3-chloro-pyridin-4-yl-amino |
| I-497 | 3-(4-chlorophenyl)-3-fluoro-allyl | 3-chloro-pyridin-4-yl-amino |
| I-498 | 3-chloro-4-fluoro-cinnamyl | 3-chloro-pyridin-4-yl-amino |

TABLE 1-continued

| Cmpd No | R⁸ | R¹ |
| --- | --- | --- |
| I-499 | 3,5-dichloro-cinnamyl | 3-chloro-pyridin-4-yl-amino |
| I-500 | 5-phenyl-penta-2,4-dienyl | 3-chloro-pyridin-4-yl-amino |
| I-501 | 4-isopropyloxycarbonylamino-cinnamyl | 3-chloro-pyridin-4-yl-amino |
| I-502 | 3-naphthalen-2-yl-allyl | 3-chloro-pyridin-4-yl-amino |
| I-503 | 3-(5-trifluoromethyl-pyridin-2-yl)-allyl | 3-chloro-pyridin-4-yl-amino |
| I-504 | 3-(5-chloro-pyridin-2-yl)-allyl | 3-chloro-pyridin-4-yl-amino |
| I-505 | 3-pyridin-4-yl-allyl | 3-chloro-pyridin-4-yl-amino |
| I-506 | 3-(2-Chloro-pyridin-4-yl)-allyl | 3-chloro-pyridin-4-yl-amino |
| I-507 | 4-chlorobenzyl | 2-methoxy-ethylamino |
| I-508 | Cinnamyl | 2-methoxy-ethylamino |
| I-509 | 4-chlorocinnamyl | 2-methoxy-ethylamino |
| I-510 | 4-fluorocinnamyl | 2-methoxy-ethylamino |
| I-511 | 4-bromocinnamyl | 2-methoxy-ethylamino |
| I-512 | 4-trifluoromethylcinnamyl | 2-methoxy-ethylamino |
| I-513 | 4-trifluoromethoxycinnamyl | 2-methoxy-ethylamino |
| I-514 | 4-pentafluoroethoxycinnamyl | 2-methoxy-ethylamino |
| I-515 | 4-methoxycinnamyl | 2-methoxy-ethylamino |
| I-516 | 4-ethoxycinnamyl | 2-methoxy-ethylamino |
| I-517 | 4-cyanocinnamyl | 2-methoxy-ethylamino |
| I-518 | 3-(6-chloro-pyridin-3-yl)-allyl | 2-methoxy-ethylamino |
| I-519 | 3-(4-chlorophenyl)-but-2-enyl | 2-methoxy-ethylamino |
| I-520 | 3-(4-chlorophenyl)-3-fluoro-allyl | 2-methoxy-ethylamino |
| I-521 | 3-chloro-4-fluoro-cinnamyl | 2-methoxy-ethylamino |
| I-522 | 3,5-dichloro-cinnamyl | 2-methoxy-ethylamino |
| I-523 | 5-phenyl-penta-2,4-dienyl | 2-methoxy-ethylamino |
| I-524 | 4-isopropyloxycarbonylamino-cinnamyl | 2-methoxy-ethylamino |
| I-525 | 3-naphthalen-2-yl-allyl | 2-methoxy-ethylamino |
| I-526 | 3-(5-trifluoromethyl-pyridin-2-yl)-allyl | 2-methoxy-ethylamino |
| I-527 | 3-(5-chloro-pyridin-2-yl)-allyl | 2-methoxy-ethylamino |
| I-528 | 3-pyridin-4-yl-allyl | 2-methoxy-ethylamino |
| I-529 | 3-(2-Chloro-pyridin-4-yl)-allyl | 2-methoxy-ethylamino |

Table II provides 529 compounds of formula Ib

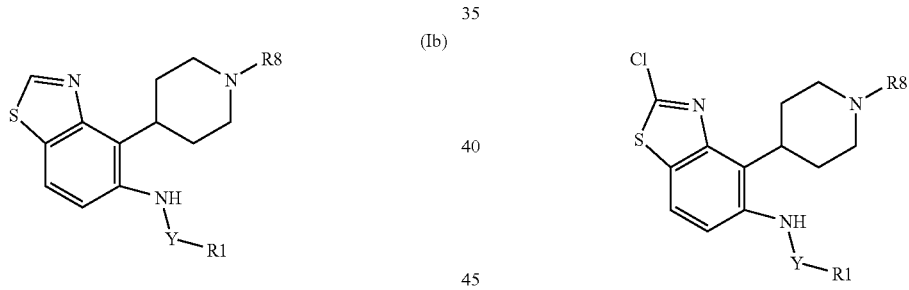

(Ib)

wherein Y is C(=O) and the values of R¹ and R⁸ are given in Table 1.

Table III provides 529 compounds of formula Ic (Ic)

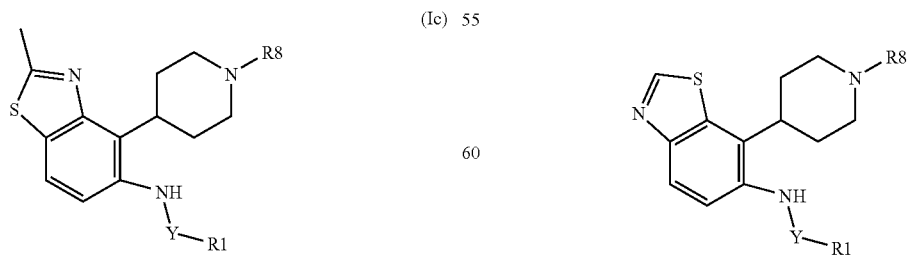

wherein Y is C(=O) and the values of R¹ and R⁸ are given in Table 1.

Table IV provides 529 compounds of formula Id (Id)

wherein Y is C(=O) and the values of R¹ and R⁸ are given in Table 1.

Table V provides 529 compounds of formula Ie (Ie)

wherein Y is C(=O) and the values of R¹ and R⁸ are given in Table 1.

Table VI provides 529 compounds of formula If

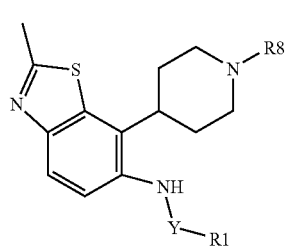
(If)

wherein Y is C(=O) and the values of R¹ and R⁸ are given in Table 1.

Table VII provides 529 compounds of formula Ig

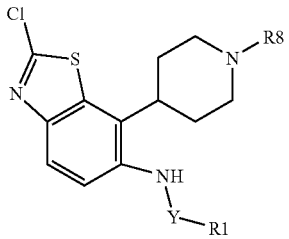
(Ig)

wherein Y is C(=O) and the values of R¹ and R⁸ are given in Table 1.

Table VIII provides 529 compounds of formula Ih

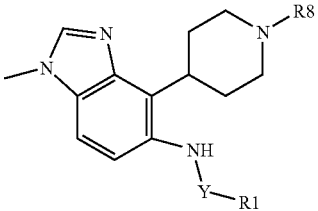
(Ih)

wherein Y is C(=O) and the values of R¹ and R⁸ are given in Table 1.

Table IX provides 529 compounds of formula Ii

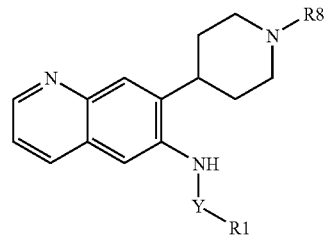
(Ii)

wherein Y is C(=O) and the values of R¹ and R⁸ are given in Table 1.

Table X provides 529 compounds of formula Ij

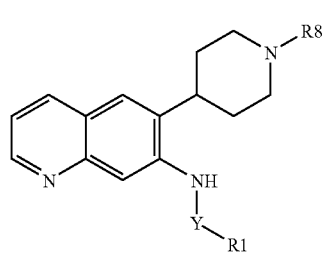
(Ij)

wherein Y is C(=O) and the values of R¹ and R⁸ are given in Table 1.

Table XI provides 529 compounds of formula Ik

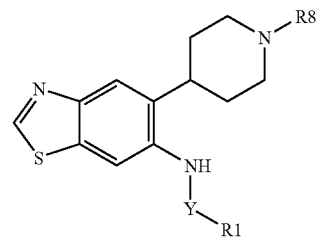
(Ik)

wherein Y is C(=O) and the values of R¹ and R⁸ are given in Table 1.

Table XII provides 529 compounds of formula Il

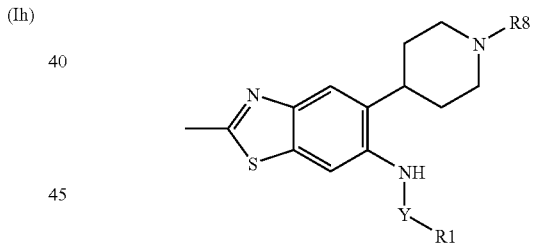
(Il)

wherein Y is C(=O) and the values of R¹ and R⁸ are given in Table 1.

Table XIII provides 529 compounds of formula Im

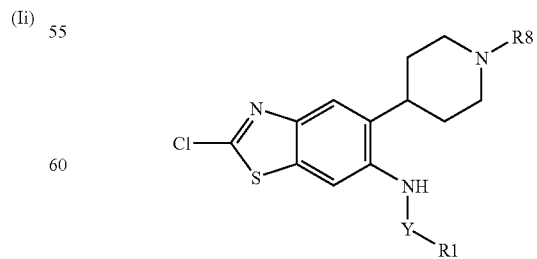
(Im)

wherein Y is C(=O) and the values of R¹ and R⁸ are given in Table 1.

Table XIV provides 529 compounds of formula In

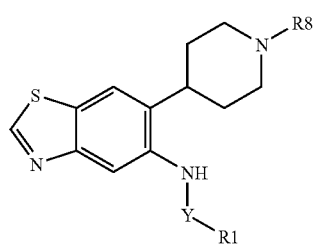

wherein Y is C(=O) and the values of R¹ and R⁸ are given in Table 1.

Table XV provides 529 compounds of formula Io

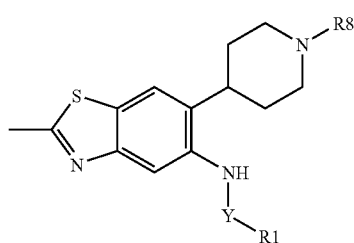

wherein Y is C(=O) and the values of R¹ and R⁸ are given in Table 1.

Table XVI provides 529 compounds of formula Ip

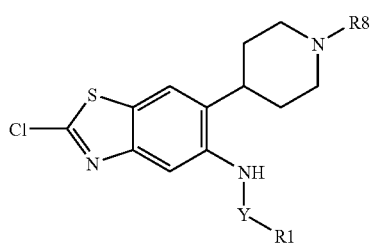

wherein Y is C(=O) and the values of R¹ and R⁸ are given in Table 1.

Table XVII provides 529 compounds of formula Iq

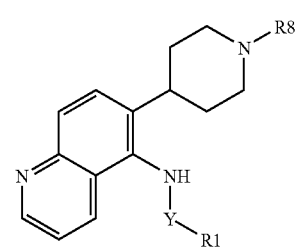

wherein Y is C(=O) and the values of R¹ and R⁸ are given in Table 1.

Table XVIII provides 529 compounds of formula Ir

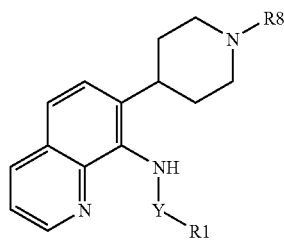

wherein Y is C(=O) and the values of R¹ and R⁸ are given in Table 1.

Table XIX provides 529 compounds of formula Is

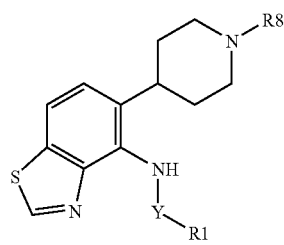

wherein Y is C(=O) and the values of R¹ and R⁸ are given in Table 1.

Table XX provides 529 compounds of formula It

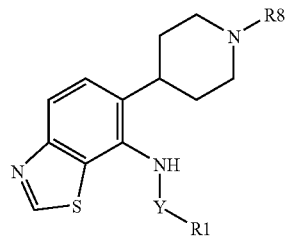

wherein Y is C(=O) and the values of R¹ and R⁸ are given in Table 1.

Table XXI provides 529 compounds of formula Iu

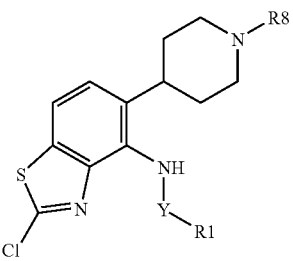

wherein Y is C(=O) and the values of R¹ and R⁸ are given in Table 1.

Table XXII provides 529 compounds of formula Iv

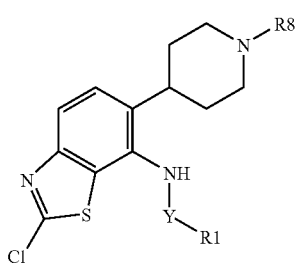

(Iv)

wherein Y is C(=O) and the values of R¹ and R⁸ are given in Table 1.

Table XXIII provides 529 compounds of formula Iw

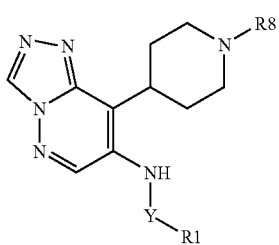

(Iw)

wherein Y is C(=O) and the values of R¹ and R⁸ are given in Table 1.

Table XXIV provides 529 compounds of formula Ix

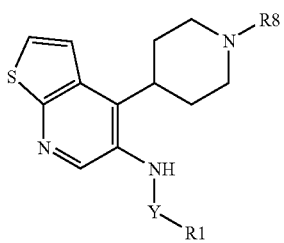

(Ix)

wherein Y is C(=O) and the values of R¹ and R⁸ are given in Table 1.

Table XXV provides 529 compounds of formula Iy

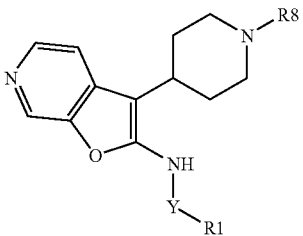

(Iy)

wherein Y is C(=O) and the values of R¹ and R⁸ are given in Table 1.

Table XXVI provides 529 compounds of formula Iz

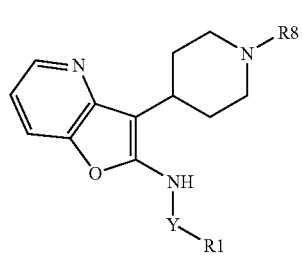

(Iz)

wherein Y is C(=O) and the values of R¹ and R⁸ are given in Table 1.

Table XXVII provides 529 compounds of formula Iaa

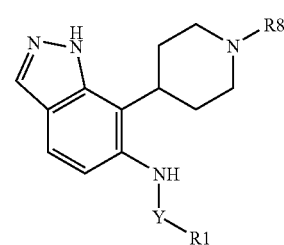

(Iaa)

wherein Y is C(=O) and the values of R¹ and R⁸ are given in Table 1.

Table XXVIII provides 529 compounds of formula Iab

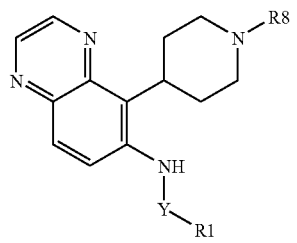

(Iab)

wherein Y is C(=O) and the values of R¹ and R⁸ are given in Table 1.

Table XXIX provides 529 compounds of formula Iac

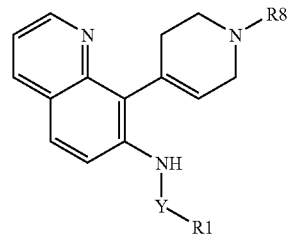

(Iac)

wherein Y is C(=O) and the values of R¹ and R⁸ are given in Table 1.

Table XXX provides 529 compounds of formula Iad

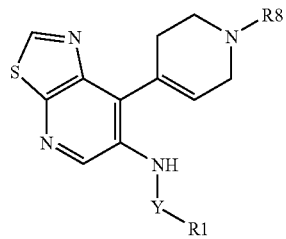
(Iad)

wherein Y is C(=O) and the values of $R^1$ and $R^8$ are given in Table 1.

Table XXXI provides 529 compounds of formula Iae

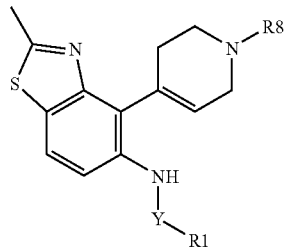
(Iae)

wherein Y is C(=O) and the values of $R^1$ and $R^8$ are given in Table 1.

The compounds of the invention may be made in a variety of ways. In the section that follows, R1, Y, R4, R8 and n are as defined under formula 1 in claim 1 unless otherwise stated.

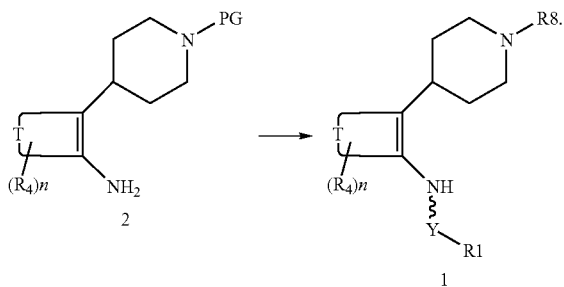

Thus compounds of general formula 1 may be derived from an intermediate of formula 2, wherein PG is R8 or a protective group using known methods to someone skilled in the art.

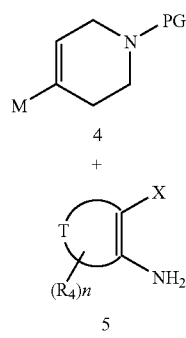

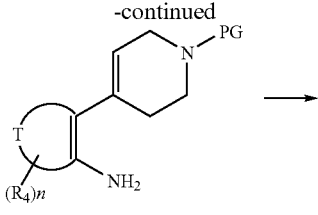

Compounds of formula 2 may be made by hydrogenation of compounds of formula 3 in the presence of a catalyst.

A Compound of formula 3 may be derived from the Suzuki or Stille coupling of a compound of formula 4 wherein M is $B(OH)_2$, $B(OC(CH_3)_2C(CH_3)O)$ or trialkyltin and a compound of formula 5 wherein X is halogen or sulfonate. Standard conditions for such a coupling involve treating 4 and 5 with a catalyst such as (tetrakistriphenylphosphine)-palladium, dichloro-bis(triphenylphosphine)palladium or dichloro[(bis-1,1'-diphenylphosphino)ferrocene]palladium (with or without an additional ligand), optionally in the presence of a base (such as sodium hydrogencarbonate, potassium carbonate, potassium phosphate or triethylamine) in a solvent such as dimethylformamide, dimethylacetamide or dioxan, optionally in the presence of water, at a temperature between room temperature and 140° C. Compounds 4 and 5 are either known or may be made by known methods to those skilled in the art.

Alternatively, a compound of formula 2 may be obtained from the Negishi coupling of a compound of formula 5 with a compound of formula 6 under standard conditions, described for example in J. Org. Chem. 2004, 69, 5120-5123. A compound of formula 6 may be made by reacting a compound of formula 7 with activated zinc as described in the same publication.

Compounds of formula 7 are either known or may be prepared by known methods to someone skilled in the art.

It must be recognised that some reagents and reaction conditions may not be compatible with certain functionalities that may be present in the molecules described. In such cases it may be necessary to employ standard protection/deprotection protocols comprehensively reported in the literature and well known to a person skilled in the art.

Also in some cases it may be necessary to perform further routine synthetic steps not described herein to complete the synthesis of the desired compounds. A person skilled in the art will also recognise that it may be possible to achieve the synthesis of the desired compounds by performing some of the steps of these synthetic routes in a different order to that described.

A person skilled in the art will also recognise that it may be possible to perform standard functional group interconversions or substitution reactions on the compounds described therein to introduce or modify substituents.

Certain compounds of formula 2 are novel and as such form a further aspect of the invention.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschisrus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeuirodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafiminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulphureus*), *Solenopsis geminata* (fire ant), *Monomorium pharaonis* (pharaoh's ant), *Damalintia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest, The compounds of formula (I) are preferably used against insects, acarines or nematodes.

The term "plant" as used herein includes seedlings, bushes and trees.

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I). The compounds of formula (I) are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr; or q) Pymetrozine.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethylbenzimidazole-1-sulphonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyanidazosulfamid), 3-5-dichloro-N-(3-chloro-1-ethyl-1-methyl-2-oxopropyl)-4-methylbenzamide (RH-7281, zoxamide), N-allyl-4,5-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples: Mass spectra data were obtained for selected compounds of the following examples using LCMS:LC5:254 nm—gradient 10% A to 100% B A=H2O+0.01% HCOOH B=CH3CN/CH3OH+0.01% HCOOH positive electrospray 150-1000 m/z.

EXAMPLE 1

This Example illustrates the preparation of 2-Chloro-N-(4-{1-[(E)-3-(4-chloro-phenyl)-allyl]-piperidin-4-yl}-benzothiazol-5-yl)-isonicotinamide II-3

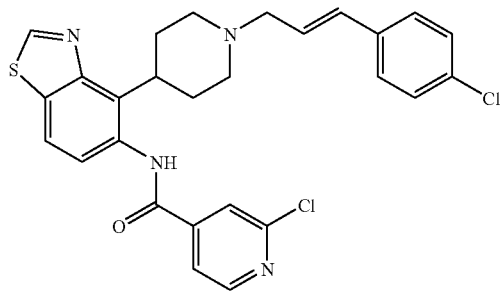

Step A 5-amino-4-bromo-benzothiazole

A stirred solution of 3 g of 5-aminobenzothiazole in 100 ml of acetonitrile at room temperature was treated with 3.5 g of N-bromosuccinimide and the resulting solution was stirred at room temperature for 4 hours. The solvent was removed under reduced pressure and the residue purified by silica gel chromatography (eluent cyclohexane/ethyl acetate 7:3) to afford 3.9 g of 5-amino-4-bromobenzothiazole as a pink solid. MS (ES+) 229/231 (MH$^+$).

Step B 4-(5-Amino-benzothiazol-4-yl)-3,6-dihydro-2H-pyridine-1-carboxylic acid tert-butyl ester A dried, argon-flushed flask was charged with 1.3 g of 4-(4,4,5,5-Tetramethyl-[1,3,2]dioxaborolan-2-yl)-3,6-dihydro-2H-pyridine-1-carboxylic acid tert-butyl ester, 1.8 g of potassium carbonate and 0.21 g of dichloro[(bis-1,1'-diphenylphosphino)ferrocene]palladium; 40 ml of dimethylformamide were added then 1 g of 5-amino-4-bromobenzothiazole and the resulting mixture was stirred at 80° C. for 18 hours. The reaction mixture was cooled to room temperature, poured into water, extracted with ethyl acetate, dried over sodium sulfate and concentrated in vacuo. Column chromatography of the residue (silica gel, cyclohexane/ethyl acetate) afforded 1.5 g of 4-(5-Amino-benzothiazol-4-yl)-3,6-dihydro-2H-pyridine-1-carboxylic acid tert-butyl ester. MS (ES+) 232 (M-BOC), 276 (M-isoprene), 332 (MH+).

Step C 4-(5-Amino-benzothiazol-4-yl)-piperidine-1-carboxylic acid tert-butyl ester 352 mg of the product obtained in step B were hydrogenated in 15 ml of methanol at 100 bar and 80° C. in the presence of 15.2 mg of 1,1'-bis(di-i-propyl-phosphino)ferrocene(1,5-cyclooctadiene)rhodium(I) tetrafluoroborate for 20 hours. After evaporation of the solvent, the residue was purified by silica gel chromatography (eluent cyclohexane/ethyl acetate 7:3) to afford 150 mg of 4-(5-Amino-benzothiazol-4-yl)-piperidine-1-carboxylic acid tert-butyl ester. MS (ES+) 234 (M-BOC), 278 (M-isoprene), 334 (MH+).

Step D

4-{5-[(2-Chloro-pyridine-4-carbonyl)-amino]-benzothiazol-4-yl}-piperidine-1-carboxylic acid tert-butyl ester 90 mg of the product obtained in step C was dissolved in 5 ml of dichloromethane; 227 mg of sodium bicarbonate was added followed by 143 mg of 2-chloroisonicotinoyl chloride and the resulting mixture was stirred at room temperature overnight. The reaction mixture was poured into diluted aqueous sodium bicarbonate, extracted with dichloromethane, dried over sodium sulfate and concentrated in vacuo to afford 144 mg of a residue, which was used directly for the next step. MS (ES+) 373/375 (M-BOC), 417/419 (M-isoprene), 473/475 (MH+).

Step E

2-Chloro-N-(4-{1-[(E)-3-(4-chloro-phenyl)-allyl]-piperidin-4-yl}-benzothiazol-5-yl)-isonicotinamide A stirred solution of 144 mg the product obtained in step D in 5 ml of dichloromethane was treated with 0.54 ml of trifluoroacetic acid the stirred at room temperature for 2 hours. The solvent was removed in vacuo and the residue dissolved in 5 ml of acetonitrile; 0.35 ml of diisopropylethylamine and 50 mg of 4-chlorocinnamyl chloride were added and the resulting mixture was stirred at room temperature overnight. The reaction mixture was poured into diluted aqueous sodium bicarbonate, extracted with diethyl ether, dried over sodium sulfate and concentrated in vacuo. Column chromatography of the residue (silica gel, ethyl acetate) afforded 20 mg of 2-chloro-N-(4-{1-[(E)-3-(4-chloro-phenyl)-allyl]-piperidin-4-yl}-benzothiazol-5-yl)-isonicotinamide as a solid. M.p. 99-103° C. $^1$H NMR (400 MHz, CDCl$_3$) 1.7 (m, 2H), 2.1 (m, 2H), 2.7 (m, 2H), 3.0 (m, 2H), 3.1 (d, J=8.5 Hz, 2H), 3.3 (m, 1H), 6.2 (dt, J=15 Hz, 8.5 Hz, 1H), 6.4 (d, J=15 Hz, 1H), 7.2 (m, 4H), 7.5 (m, 1H), 7.7 (m, 1H), 7.8 (d, J=10 Hz, 1H), 7.8 (s, 1H), 8.1 (s, 1H), 8.5 (m, 1H), 8.9 (s, 1H); MS (ES) 523/525 (MH+).

The following compounds were prepared according to procedures analogous to those described in Example 1:

| Cpd N° | Compound Structure | MH+ Electrospray | M.p (° C.) |
|---|---|---|---|
| II-7 | 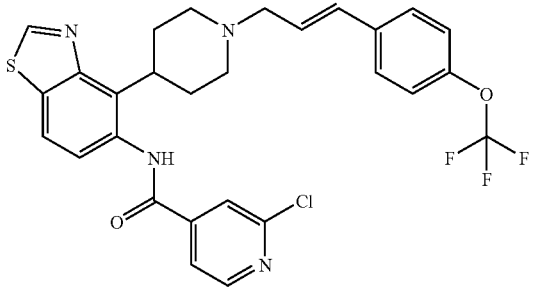 | 573/575 | |
| II-5 | 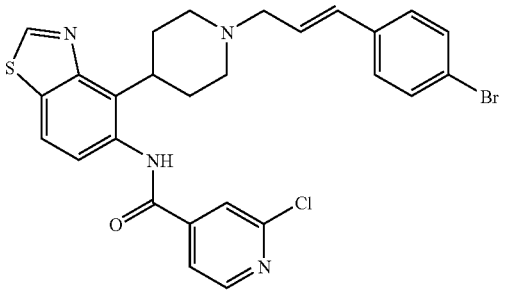 | 567/569/571 | |
| XXXI-3 | 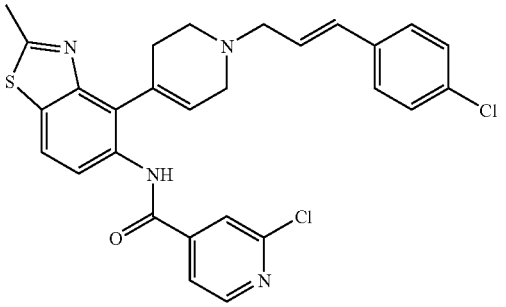 | 535/537 | 73-76° C. |
| I-3 | 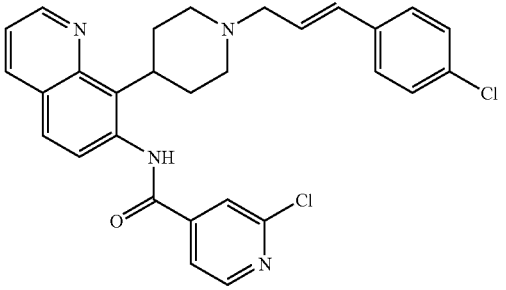 | 517/519 | |
| XXIX-3 | 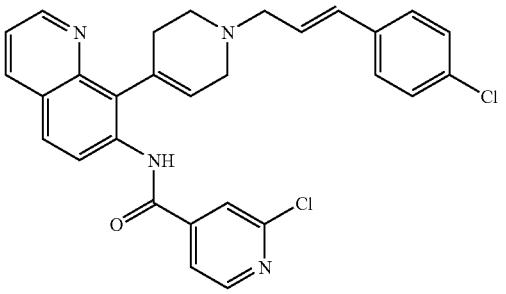 | 515/517 | |

| Cpd N° | Compound Structure | MH+ Electrospray | M.p (° C.) |
|---|---|---|---|
| V-3 | 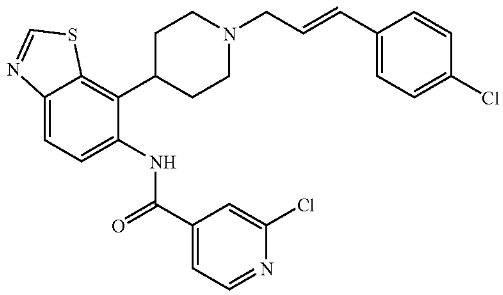 | 523/525 | |
| XXVII-3 | 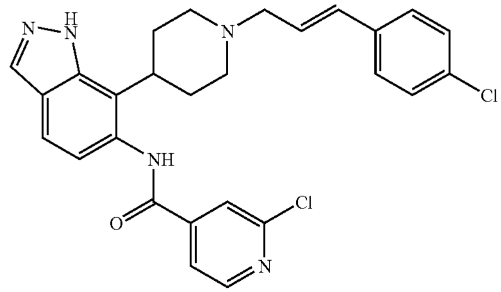 | 506/508 | |
| XXVIII-3 | 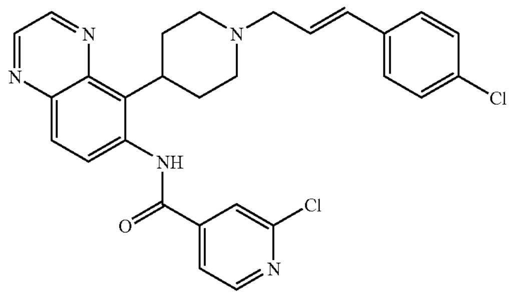 | 518/520 | 98-100° C. |

EXAMPLE 2

This Example illustrates the pesticidal/insecticidal properties of compounds of formula (I). Test against were performed as follows:

*Spodoptera littoralis* (Egyptian Cotton Leafworm)

Cotton leaf discs were placed on agar in a 24-well microtiter plate and sprayed with test solutions at an application rate of 200 ppm. After drying, the leaf discs were infested with 5 $L_1$ larvae. The samples were checked for mortality, repellent effect, feeding behaviour, and growth regulation 3 days after treatment (DAT). The following compounds gave at least 80% control of *Spodoptera littoralis*: I-3, II-3, II-7, V-3, XXVII-3, XXVIII-3, XXIX-3, XXXI-3.

*Heliothis virescens* (Tobacco Budworm):

Eggs (0-24 h old) were placed in 24-well microtiter plate on artificial diet and treated with test solutions at an application rate of 200 ppm by pipetting. After an incubation period of 4 days, samples were checked for egg mortality, larval mortality, and growth regulation. The following compounds gave at least 80% control of *Heliothis virescen*: I-3, II-3, II-7, V-3, XXVIII-3, XXIX-3, XXXI-3.

*Plutella xylostella* (Diamond Back Moth):

24-well microtiter plate (MTP) with artificial diet was treated with test solutions at an application rate of 18.2 ppm by pipetting. After drying, the MTP's were infested with larvae (L2) (10-15 per well). After an incubation period of 5 days, samples were checked for larval mortality, antifeedant and growth regulation. The following compounds gave at least 80% control of *Plutella xylostella*: I-3, II-3, II-7, XXVII-3.

*Diabrotica balteata* (Corn Root Worm):

A 24-well microtiter plate (MTP) with artificial diet was treated with test solutions at an application rate of 200 ppm (concentration in well 18 ppm) by pipetting. After drying, the MTP's were infested with larvae (L2) (6-10 per well). After an incubation period of 5 days, samples were checked for larval mortality, and growth regulation. The following compounds gave at least 80% control of *Diabrotica balteata*: I-3, II-7, XXVIII-3.

*Aedes aegypti* (Yellow Fever Mosquito):

10-15 *Aedes* larvae (L2) together with a nutrition mixture are placed in 96-well microtiter plates. Test solutions at an application rate of 2 ppm are pipetted into the wells. 2 days later, insects were checked for mortality and growth inhibition. The following compounds gave at least 80% control of *Aedes aegypti*: I-3, II-3, II-7, V-3, XXVII-3, XXVIII-3, XXIX-3, XXXI-3.

The invention claimed is:

1. A method of combating and controlling insects, said method comprising applying to an insect, to a locus of an insect, or to a plant susceptible to attack by an insect, an insecticidally effective amount of a compound of formula (I):

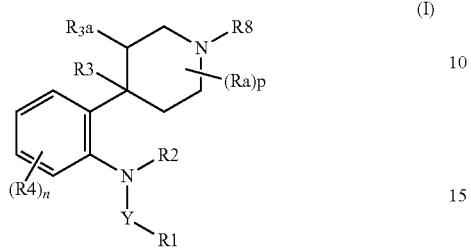

wherein:
Y is a single bond, C=O, C=S or S(O)$_m$;
m is 0, 1 or 2;
$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$;
$R^{13}$ and $R^{14}$ are each independently hydrogen, $COR^{15}$, optionally substituted alkyl, optionally substituted aryl, optionally substituted heteroaryl, or optionally substituted heterocyclyl; or $R^{13}$ and $R^{14}$ together with the N atom to which they are attached form a group —N=C($R^{16}$)—$NR^{17}R^{18}$; or $R^{13}$ and $R^{14}$ together with the N atom to which they are attached form a five, six or seven-membered heterocyclic ring which may contain one or two further heteroatoms selected from O, N or S and which may be optionally substituted by one or two $C_{1-6}$ alkyl groups;
$R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$;
$R^{16}$, $R^{17}$ and $R^{18}$ are each independently H or lower alkyl;
$R^{19}$ and $R^{20}$ are each independently optionally substituted alkyl, optionally substituted aryl or optionally substituted heteroaryl;
$R^2$ is H, hydroxy, optionally substituted alkoxy or optionally substituted alkyl;
or $R^1$ and $R^2$ together with the groups Y and N form a 5- or 6-membered heterocyclic ring which may optionally contain one further heteroatom selected from O, N or S and which may be optionally substituted by $C_{1-4}$ alkyl, $C_{1-4}$ haloalkyl or halogen;
$R^3$ is H, OH, halogen or optionally substituted alkyl;
$R^{3a}$ is H or $R^3$ and $R^{3a}$ together form a bond;
two adjacent groups $R^4$ together with the atoms to which they are attached form a 4, 5, 6, or 7 membered heteroaromatic, or heterocyclic ring optionally carrying one, two or three $R^5$ groups; provided that when the two adjacent $R^4$ groups are both attached to carbon atoms to form a heterocyclic ring, the resulting heterocyclic ring is substituted with a substituent other than (i) halogen, (ii) $C_{1-8}$ alkoxy, (iii) $C_{1-6}$ haloalkoxy, (iv) phenoxy optionally substituted by halo, nitro, cyano, $C_{1-6}$ alkyl, $C_{1-6}$ haloalkyl, $C_{1-6}$ alkoxy or $C_{1-6}$ haloalkoxy, (v) heteroaryloxy optionally substituted by halo, nitro, cyano, $C_{1-6}$ alkyl, $C_{1-6}$ haloalkyl, $C_{1-6}$ alkoxy or $C_{1-6}$ haloalkoxy, (vi) $C_{1-8}$ alkylthio or (vii) $R^{19}R^{20}N$;
$R^{19}$ and $R^{20}$ are each independently hydrogen, $C_{1-8}$ alkyl, $C_{3-7}$ cycloalkyl, $C_{3-6}$ alkenyl, $C_{3-6}$ alkynyl, $C_{2-6}$ haloalkyl, or $C_{1-6}$ alkoxycarbonyl or $R^{19}$ and $R^{20}$ together with the N atom to which they are attached form a five, six or seven-membered heterocyclic ring which may contain one or two further heteroatoms selected from O, N or S and which may be optionally substituted by one or two $C_{1-6}$ alkyl groups;
optionally any further $R^4$ groups are each independently halogen, nitro, cyano, thiocyanato, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, arylthio, heteroarylthio, alkylsulfoxyl, arylsulfoxyl, heteroarylsulfoxyl, alkylsulfonyl, arylsulfonyl, heteroarylsulfonyl or $R^{23}R^{24}N$;
$R^{23}$ and $R^{24}$ are each independently hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$alkyl, $C_{2-6}$ haloalkyl, $C_{1-6}$ alkoxy ($C_{1-6}$)alkyl, or $C_{1-6}$ alkoxycarbonyl; or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups;
n is 2, 3 or 4
each $R^5$ is independently halogen, nitro, cyano, thiocyanato, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, arylthio, heteroarylthio, alkylsulfoxyl, arylsulfoxyl, heteroarylsulfoxyl, alkylsulfonyl, arylsulfonyl, heteroarylsulfonyl or $R^{25}R^{26}N$;
$R^{25}$ and $R^{26}$ are each independently hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$alkyl, $C_{2-6}$ haloalkyl, $C_{1-6}$ alkoxy ($C_{1-6}$)alkyl, $C_{1-6}$ alkoxycarbonyl or $R^{25}$ and $R^{26}$ together with the N atom to which they are attached form a five, six or seven-membered heterocyclic ring which may contain one or two further heteroatoms selected from O, N or S and which may be optionally substituted by one or two $C_{1-6}$ alkyl groups;

R$^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl;

each Ra is independently halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or R$^{29}$R$^{30}$N;

R$^{29}$ and R$^{30}$ are each independently hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$alkyl, $C_{2-6}$ haloalkyl, $C_{1-6}$ alkoxy ($C_{1-6}$)alkyl, or $C_{1-6}$ alkoxycarbonyl; or R$^{29}$ and R$^{30}$ together with the N atom to which they are attached form a five, six or seven-membered heterocyclic ring which may contain one or two further heteroatoms selected from O, N or S and which may be optionally substituted by one or two $C_{1-6}$ alkyl groups;

or two Ra groups attached to the same carbon atom are =O, =S, =NRb, =CRcRd;

Rb, Rc and Rd are each independently H or optionally substituted alkyl; and p is 0, 1, 2, 3 or 4;

or salts or N-oxides thereof.

2. A method according to claim 1 wherein two adjacent groups R$^4$ together with the atoms to which they are attached form a 5,6 or 6,6 fused heteroaromatic or heterocyclic ring wherein the ring members are each independently CH, S, N, NR$^5$, O, or CR$^5$ provided that there are no more than one O or S atoms present in the ring.

3. A method according to claim 1 wherein:

R$^8$ is (i) $C_{1-10}$ alkyl, (ii) $C_{1-10}$ haloalkyl, (iii) aryl($C_{1-6}$)alkyl wherein the aryl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, (iv) heteroaryl($C_{1-6}$)alkyl wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, (v) arylcarbonyl-($C_{1-6}$)alkyl wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino and the alkyl group may be optionally substituted by aryl, (vi) $C_{2-8}$ alkenyl, (vii) $C_{2-8}$ haloalkenyl, (viii) aryl($C_{2-6}$)-alkenyl wherein the aryl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring, (ix) heteroaryl($C_{2-6}$)-alkenyl wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring, (x) $C_{2-6}$ alkynyl, (xi) phenyl($C_{2-6}$)alkynyl wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, (xi) $C_{3-7}$ cycloalkyl, (xii) $C_{1-6}$ alkoxycarbonyl, (xiii) $C_{1-6}$ alkylcarbonyl, (xiv) $C_{1-6}$ haloalkylcarbonyl (xv) aryl($C_{2-6}$)alkenylcarbonyl wherein the aryl group may be optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, or (xvi) —C(R$^{51}$)(R$^{52}$)—[CR$^{53}$=CR$^{54}$]z-R$^{55}$;

z is 1 or 2;

R$^{51}$ and R$^{52}$ are each independently H, halo or $C_{1-2}$ alkyl;

R$^{53}$ and R$^{54}$ are each independently H, halogen, $C_{1-4}$ alkyl or $C_{1-4}$ haloalkyl; and R$^{55}$ is optionally substituted aryl or optionally substituted heteroaryl.

4. A method according to claim 1 wherein Y is a single bond, C=O or C=S.

5. A method according to 1 wherein:

R$^1$ is (i) hydrogen, (ii) $C_{1-6}$ alkyl, (iii) $C_{1-6}$ cyanoalkyl, (iv) $C_{1-6}$ haloalkyl, (v) $C_{3-7}$ cycloalkyl($C_{1-4}$)alkyl, (vi) $C_{1-6}$ alkoxy($C_{1-6}$)alkyl, (vii) heteroaryl($C_{1-6}$)alkyl wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen, (viii) aryl($C_{1-6}$)alkyl wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen, (ix) $C_{1-6}$ alkylcarbonylamino($C_{1-6}$)alkyl, (x) aryl which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen, (xi) heteroaryl which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen, (xii) $C_{1-6}$ alkoxy, (xiii) $C_{1-6}$ haloalkoxy, (xiv) phenoxy wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, (xv) heteroaryloxy optionally substituted by halo, nitro, cyano, $C_{1-6}$ alkyl, $C_{1-6}$ haloalkyl, $C_{1-6}$ alkoxy or $C_{1-6}$ haloalkoxy, (xvi) heterocyclyloxy optionally substituted by halo, $C_{1-6}$ alkyl, $C_{1-6}$ haloalkyl, $C_{1-6}$ alkoxy or $C_{1-6}$ haloalkoxy, (xvii) cyano, (xviii) $C_{2-6}$ alkenyl, (xix) $C_{2-6}$ alkynyl, (xx) $C_{3-6}$ cycloalkyl, (xxi) $C_{5-7}$ cycloalkenyl, (xxii) heterocyclyl optionally substituted by halo, nitro, cyano, $C_{1-6}$ alkyl, $C_{1-6}$ haloalkyl, $C_{1-6}$ alkoxy or $C_{1-6}$ haloalkoxy, (xxiii) $C_{1-6}$ alkylthio, (xxiv) $C_{1-6}$ haloalkylthio or (xxv) $NR^{13}R^{14}$;

$R^{13}$ and $R^{14}$ are each independently (i) hydrogen, (ii) $C_{1-6}$ alkyl, (iii) $C_{1-6}$ haloalkyl, (iv) $C_{1-6}$ alkoxy($C_{1-6}$)alkyl, (v) phenyl which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino or $C_{1-4}$ alkoxycarbonyl, (vi) phenyl ($C_{1-6}$)alkyl wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen, (vii) heteroaryl ($C_{1-6}$)alkyl wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen or (viii) heteroaryl which may be optionally substituted by (a) halo, (b) nitro, (c) cyano, (d) $C_{1-6}$ alkyl, (e) $C_{1-6}$ haloalkyl, (f) $C_{1-6}$ alkoxy, (g) $C_{1-6}$ haloalkoxy, (h) $C_{1-4}$ alkoxycarbonyl, (i) $C_{1-6}$ alkylcarbonylamino, (j) phenyloxycarbonylamino wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, (k) amino, (l) $C_{1-6}$ alkylamino or (m) phenylamino wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

6. A method according to claim 1 wherein $R^2$ is hydrogen, hydroxy, $C_{1-6}$ alkyl or $C_{1-6}$ haloalkyl.

7. A method according to claim 1 wherein $R^3$ is hydrogen, hydroxy, halogen, $C_{1-6}$ alkyl or $C_{1-6}$ haloalkyl, and $R^{3a}$ is hydrogen; or $R^3$ and $R^{3a}$ together form a double bond.

8. A method according to claim 1 wherein each Ra is independently fluoro, methyl, or hydroxyl; or two Ra groups together with the carbon atom to which they are attached form a carbonyl group; and p is 0, 1 or 2.

9. A method according to claim 1 wherein two adjacent groups $R^4$ together with the atoms to which they are attached form a 4, 5, 6, or 7 membered heteroaromatic or heterocyclic ring optionally carrying one, two or three $R^5$ groups.

10. A method according to claim 9 wherein two adjacent groups $R^4$ together with the atoms to which they are attached form a 5 or 6 membered heteroaromatic or heterocyclic ring optionally carrying one, two or three $R^5$ groups.

11. A method according to claim 10 wherein two adjacent groups $R^4$ together with the atoms to which they are attached form a 5 membered heteroaromatic or heterocyclic ring optionally carrying one, two or three $R^5$ groups.

12. A method according to claim 1 wherein:

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$; and $R^2$ is H, hydroxy, optionally substituted alkoxy or optionally substituted alkyl.

13. A method according to claim 12 wherein $R^2$ is H.

14. A method according to claim 4 wherein Y is C=O.

* * * * *